United States Patent
Kim

(10) Patent No.: US 7,501,416 B2
(45) Date of Patent: Mar. 10, 2009

(54) QUINOXALINE COMPOUNDS AND METHODS OF USING THEM

(75) Inventor: Kyoung S. Kim, North Brunswick, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 593 days.

(21) Appl. No.: 11/047,787

(22) Filed: Feb. 1, 2005

(65) Prior Publication Data

US 2005/0176717 A1    Aug. 11, 2005

Related U.S. Application Data

(60) Provisional application No. 60/542,489, filed on Feb. 6, 2004.

(51) Int. Cl.
| | |
|---|---|
| A01N 43/58 | (2006.01) |
| A01N 43/60 | (2006.01) |
| A61K 31/50 | (2006.01) |
| A61K 31/495 | (2006.01) |
| C07D 401/00 | (2006.01) |
| C07D 403/00 | (2006.01) |
| C07D 405/00 | (2006.01) |
| C07D 409/00 | (2006.01) |
| C07D 411/00 | (2006.01) |
| C07D 413/00 | (2006.01) |
| C07D 417/00 | (2006.01) |
| C07D 419/00 | (2006.01) |
| C07D 239/02 | (2006.01) |

(52) U.S. Cl. ..................... 514/249; 544/333; 544/334
(58) Field of Classification Search ............... None
See application file for complete search history.

(56) References Cited

FOREIGN PATENT DOCUMENTS

| EP | 0 288 898 | 4/1988 |
|---|---|---|
| WO | WO 99/26927 | 6/1999 |
| WO | WO 99/42461 | 8/1999 |
| WO | WO 00/42026 | 7/2000 |

OTHER PUBLICATIONS

Blatt, et al., Journal of the American Chemical Society (1936), 58, 1894-9.*
Weinstock, et. al., Journal of the American Chemical Society (1936) 58, 1986-8.*
Vippagunta et. al. Advanced Drug Delivery Reviews 48 (2001) 3-26.*
Dahn, et. al., Helvetica Chimica Acta (1960), 43, 1555-61.*
Landquist, J.K. et al., "Quinoxaline N-Oxides. Part II.* Oxides of Py-Substituted Quinoxalines", J. Chem. Soc., Abstracts, pp. 2822-2830 (1953).
Huber, B. et al., "Formation of 1-amino-1,4-dideoxy-2,3-hexodiuloses and 2-aminoacetylfurans in the Maillard reaction", Carbohydrate Research, vol. 204, pp. 215-220 (1990).
Search Report "A".

* cited by examiner

*Primary Examiner*—James O Wilson
*Assistant Examiner*—Jeffrey H Murray
(74) *Attorney, Agent, or Firm*—Anastasia P. Winslow; Maureen S. Gibbons

(57) ABSTRACT

The present invention generally relates to quinoxaline compounds having Formula 1 or Formula 2 wherein the variables are as defined herein, and methods of using them.

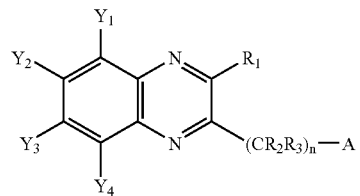

Formula 1

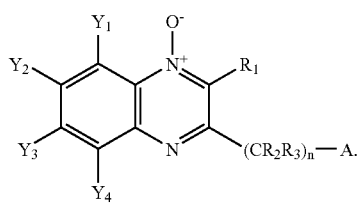

Formula 2

16 Claims, No Drawings

QUINOXALINE COMPOUNDS AND METHODS OF USING THEM

RELATED APPLICATIONS

This application claims priority benefit under Title 35 § 119(e) of U.S. provisional Application No. 60/542,489, filed Feb. 6, 2004, the contents of which are herein incorporated by reference.

BACKGROUND OF THE INVENTION

The present invention generally relates to quinoxaline compounds and methods of using them.

Cell proliferation and programmed cell death play important roles in the growth and development of an organism. In proliferative diseases such as cancer, the processes of cell proliferation and/or programmed cell death are often perturbed. For example, a cancer cell may have unregulated cell division through either the overexpression of a positive regulator of the cell cycle or the loss of a negative regulator of the cell cycle, perhaps by mutation. Alternatively, a cancer cell may have lost the ability to undergo programmed cell death through the overexpression of a negative regulator of apoptosis.

One approach to the treatment of human cancers is to target a protein that is essential for cell cycle progression. In order for the cell cycle to proceed from one phase to the next, certain prerequisite events must be completed. There are checkpoints within the cell cycle that enforce the proper order of events and phases. One such checkpoint is the spindle checkpoint that occurs during the metaphase stage of mitosis. Small molecules that target proteins with essential functions in mitosis have the potential to initiate the spindle checkpoint to arrest cells in mitosis. Of the small molecules that arrest cells in mitosis, the majority of those which display anti-tumor activity in the clinic also induce apoptosis. Most compounds known to cause mitotic arrest and apoptosis act as tubulin binding agents. These compounds are believed to alter the dynamic instability of microtubules and indirectly alter the function/structure of the mitotic spindle, thereby causing mitotic arrest. Because most of these compounds target the tubulin protein, a component of all microtubules, they can also affect normal cellular processes in which microtubules have a role.

In view of the foregoing, a need exists for small molecules that target proteins associated with proliferating cells.

SUMMARY OF THE INVENTION

The present invention provides quinoxaline compounds and methods of using them to, for example, inhibit cell proliferation. In certain embodiments, quinoxaline compounds of the invention are those of Formula 1 and 2.

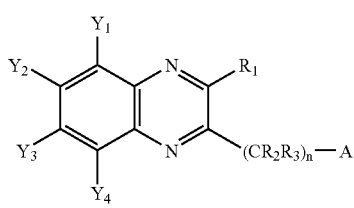

Formula 1

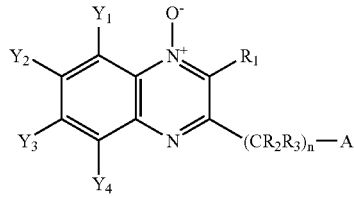

Formula 2 wherein:
$Y_1$, $Y_2$, $Y_3$ and $Y_4$ are independently hydrogen, halogen, —CN, alkyl, cycloalkyl, alkenyl, alkynyl, aryl, heteroaryl, —$OR_6$, —$NR_7R_8$, —$C(=O)R_9$, —$C(=O)OR_{10}$, —$C(=O)NR_{11}R_{12}$, —$OC(=O)OR_{10}$, —$OC(=O)NR_{11}R_{12}$, —$NR_{13}C(=O)OR_{10}$, —$NR_{13}C(=O)NR_{11}R_{12}$, —$SO_2R_9$, —$SO_2NR_{11}R_{12}$, or —$NR_{13}SO_2NR_{11}R_{12}$;

$R_1$ is alkyl, cycloalkyl, alkenyl, alkynyl, aryl, heteroaryl, aralkyl, or heteroarylalkyl;

$R_2$ and $R_3$ are independently hydrogen, halogen, alkyl, cycloalkyl, alkenyl, alkynyl, aryl, heteroaryl, or $R_2$ and $R_3$ are taken together to form a carbocyclic or heterocyclic ring of 3 to 8 atoms;

n is from 1 to 4;

A is $O(R_4)$, $S(R_4)$ or $N(R_4)(R_5)$;

$R_4$ is hydrogen, alkyl, cycloalkyl, alkenyl, alkynyl, aryl, heteroaryl, aralkyl, $(CH_2)_mNR^9R^{10}$, $(CH_2)_mC(=O)NR^9R^{10}$; or $(CH_2)_mC(=O)OR^{20}$;

$R_5$ is $C(=O)R_9$, $C(=O)OR_{10}$, $C(=O)NR_{11}R_{12}$, $SO_2R_9$, or $SO_2NR_{11}R_{12}$;

or $R_4$ and $R_5$ are taken together to form a carbocyclic or heterocyclic ring of 3 to 8 atoms;

m is from 1 to 5;

$R_6$, $R_7$, and $R_8$ are independently hydrogen, alkyl, cycloalkyl, alkenyl, alkynyl, aryl, heteroaryl, —$C(=O)H$, —$C(=O)$alkyl, —$C(=O)$alkenyl, —$C(=O)$alkynyl, —$C(=O)$aryl, —$C(=O)$heteroaryl, or $R_7$ and $R_8$ are taken together to form a carbocyclic or heterocyclic ring of 3 to 8 atoms;

$R_9$, $R_{10}$, $R_{11}$, $R_{12}$, $R_{13}$ are independently hydrogen, alkyl, cycloalkyl, alkenyl, alkynyl, aryl, heteroaryl, or $R_{11}$ and $R_{12}$ are taken together to form a carbocyclic or heterocyclic ring of 3 to 8 atoms; and $R^{20}$ is hydrogen or alkyl.

The present invention also provides, inter alia, solvates, hydrates and pharmaceutically acceptable salt or ester forms of compounds of Formula 1 and Formula 2.

Methods of using quinoxaline compounds also are provided. In one aspect, a pharmaceutically effective amount of one or more quinoxaline compound is administered to a subject suspected to be in need of an inhibition of cell proliferation. In some embodiments, the method will inhibit tumor cell proliferation in the subject and/or induce tumor regression in the subject and/or arrest tumor growth in the subject.

The present invention further provides, inter alia, methods of inducing apoptosis in a subject. In one aspect, a pharmaceutically effective amount of one or more quinoxaline compound is administered to a subject suspected to be in need thereof. In some embodiments, the method will inhibit tumor cell proliferation in the subject and/or induce tumor regression in the subject and/or arrest tumor growth in the subject.

The present invention also provides, inter alia, methods of inducing cell cycle arrest comprising administering to a population of cells a compound of the present invention. The cell population can be an in vitro population of cells or an in vivo population of cells. In one aspect, the cells are tumor cells.

The methods of the present invention also include methods for inducing cytotoxicity in a subject, modulating Eg5 in a subject, and/or treating diseases or disorders such as those diseases or disorders characterized by abnormal cell proliferation. Such methods comprise administering to a subject suspected to be in need thereof a pharmaceutically effective amount of a quinoxaline compound of the present invention. In one aspect the disease is cancer. In another aspect the disease or disorder is autoimmune disease, fungal disease, viral disease, neurodegenerative disease, and cardiovascular disease.

The present invention also provides, inter alia, methods of determining the activity of a compound of the present invention. The method can include the step of contacting a compound of the present invention with a motor protein and further determining the activity of the motor protein, for example, by monitoring cell proliferation. The step of determining the activity of the motor protein can occur before or after the contacting step. In one aspect, the motor protein is Eg5.

The present invention also provides, inter alia, kits for inhibiting cell proliferation and/or for treating cancer in a subject comprising a container, a pharmaceutical composition contained therein comprising a quinoxaline compound of the present invention, and a package insert indicating that the pharmaceutical composition can be used for the inhibition of cell proliferation and/or for the treatment of cancer.

DETAILED DESCRIPTION OF THE INVENTION

Compounds of the present invention include those of Formula 1 and Formula 2:

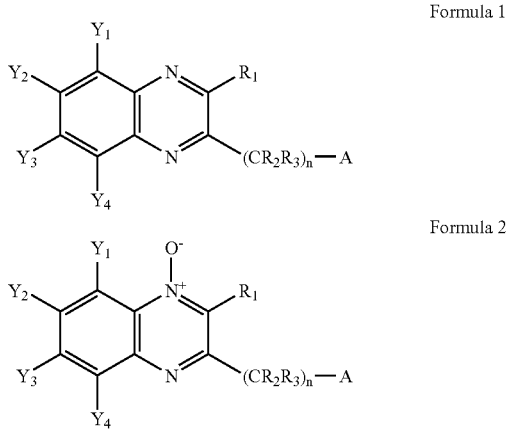

wherein:
$Y_1$, $Y_2$, $Y_3$ and $Y_4$ are independently hydrogen, halogen, —CN, alkyl, cycloalkyl, alkenyl, alkynyl, aryl, heteroaryl, —$OR_6$, —$NR_7R_8$, —C(=O)$R_9$, —C(=O)$OR_{10}$, —C(=O)$NR_{11}R_{12}$, —OC(=O)$OR_{10}$, —OC(=O)$NR_{11}R_{12}$, —$NR_{13}$C(=O)$OR_{10}$, —$NR_{13}$C(=O)$NR_{11}R_{12}$, —$SO_2R_9$, —$SO_2NR_{11}R_{12}$, or —$NR_{13}SO_2NR_{11}R_{12}$;

$R_1$ is alkyl, cycloalkyl, alkenyl, alkynyl, aryl, heteroaryl, aralkyl, or heteroarylalkyl;

$R_2$ and $R_3$ are independently hydrogen, halogen, alkyl, cycloalkyl, alkenyl, alkynyl, aryl, heteroaryl, or $R_2$ and $R_3$ are taken together to form a carbocyclic or heterocyclic ring of 3 to 8 atoms;

n is from 1 to 4;

A is O($R_4$), S($R_4$) or N($R_4$)($R_5$);

$R_4$ is hydrogen, alkyl, cycloalkyl, alkenyl, alkynyl, aryl, heteroaryl, aralkyl, $(CH_2)_mNR^9R^{10}$, $(CH_2)_mC(=O)NR^9R^{10}$; or $(CH_2)_mC(=O)OR^{20}$;

$R_5$ is C(=O)$R_9$, C(=O)$OR_{10}$, C(=O)$NR_{11}R_{12}$, $SO_2R_9$, or $SO_2NR_{11}R_{12}$;

or $R_4$ and $R_5$ are taken together to form a carbocyclic or heterocyclic ring of 3 to 8 atoms;

m is from 1 to 5;

$R_6$, $R_7$, and $R_8$ are independently hydrogen, alkyl, cycloalkyl, alkenyl, alkynyl, aryl, heteroaryl, —C(=O)H, —C(=O)alkyl, —C(=O)alkenyl, —C(=O)alkynyl, —C(=O)aryl, —C(=O)heteroaryl, or $R_7$ and $R_8$ are taken together to form a carbocyclic or heterocyclic ring of 3 to 8 atoms;

$R_9$, $R_{10}$, $R_{11}$, $R_{12}$, $R_{13}$ are independently hydrogen, alkyl, cycloalkyl, alkenyl, alkynyl, aryl, heteroaryl, or $R_{11}$ and $R_{12}$ are taken together to form a carbocyclic or heterocyclic ring of 3 to 8 atoms;

and $R_{20}$ is hydrogen or alkyl.

The present invention also provides, inter alia, enantiomers, diastereomers, pharmaceutically acceptable salts and esters, prodrugs and solvates of Formula 1 and Formula 2.

In some embodiments of the present invention, compounds of Formulas 1 and 2 include those wherein $Y_1$, $Y_2$, $Y_3$ and $Y_4$ are, independently, hydrogen, halogen, —CN, alkyl, cycloalkyl, alkenyl, alkynyl, aryl, heteroaryl, —$OR_6$, —$NR_7R_8$, —C(=O)$R_9$, C(=O)$OR_{10}$, —C(=O)$NR_{11}R_{12}$, —OC(=O)$OR_{10}$, —OC(=O)$NR_{11}R_{12}$, —$NR_{13}$C(=O)$OR_{10}$, —$NR_{13}$C(=O)$NR_{11}R_{12}$, —$SO_2R_9$, —$SO_2NR_{11}R_{12}$, or —$NR_{13}SO_2NR_{11}R_{12}$, wherein the alkyl, cycloalkyl, alkenyl, alkynyl, aryl, and heteroaryl groups are optionally substituted as defined herein. In a particularly preferred embodiment of Formulas 1 and 2, $Y_1$, $Y_2$, $Y_3$ and $Y_4$ are hydrogen or halogen. For example, in some embodiments, $Y_1$, $Y_2$, and $Y_4$ are hydrogen and $Y_3$ is halogen or $Y_1$, $Y_2$, and $Y_4$ are hydrogen and $Y_3$ is chlorine.

In some embodiments, compounds of Formulas 1 and 2 include those wherein $R_1$ is alkyl, cycloalkyl, alkenyl, alkynyl, aryl, heteroaryl, aralkyl, or heteroarylalkyl, wherein the alkyl, cycloalkyl, alkenyl, alkynyl, aryl, heteroaryl, aralkyl, and heteroarylalkyl groups are optionally substituted as defined herein. In a particularly preferred embodiment, $R_1$ is aralkyl or alkyl. For example in some embodiments, $R_1$ is benzyl or methyl.

In some embodiments, compounds of Formulas 1 and 2 include those wherein $R_2$ and $R_3$ are independently hydrogen, halogen, alkyl, cycloalkyl, alkenyl, alkynyl, aryl, heteroaryl, wherein the alkyl, cycloalkyl, alkenyl, alkynyl, aryl, or heteroaryl groups are optionally substituted as defined herein or $R_2$ and $R_3$ are taken together to form a carbocyclic or heterocyclic ring of 3 to 8 atoms. In preferred embodiments, $R_2$ and $R_3$ are taken together to form a carbocyclic ring of from 3 to 8 atoms. For example, in some embodiments, $R_2$ and $R_3$ are taken together to form cyclopropane.

Preferred compounds of Formulas 1 and 2 include those wherein n is 1.

In some embodiments, compounds of Formulas 1 and 2 include those wherein $R_4$ is alkyl, cycloalkyl, alkenyl, alkynyl, aryl, heteroaryl, aralkyl, $(CH_2)_mNR^9R^{10}$, $(CH_2)_mC(=O)NR^9R^{10}$ or $(CH_2)_mC(=O)OR^2$ wherein n is 1, 2, 3, 4, or 5 and wherein the alkyl, cycloalkyl, alkenyl, alkynyl, aryl, and heteroaryl groups are optionally substituted as defined herein. In preferred embodiments, $R_4$ is $(CH_2)_m NR^9 R^{10}$, or $(CH_2)_m C(=O)NR^9R^{10}$ wherein m is 1, 2, 3, 4, or 5. For example, in some preferred embodiments, $R_4$ is $(CH_2)_m NH_2$ or $(CH_2)_m C(=O)NH_2$. In a particularly preferred embodiment, $R_4$ is $(CH_2)_3 NH_2$ or $(CH_2)_3 C(=O)NH_2$.

In some embodiments, compounds of Formulas 1 and 2 include those wherein $R_5$ is $C(=O)R_9$, $C(=O)OR_{10}$, $C(=O)NR_{11}R_{12}$, $SO_2R_9$, or $SO_2NR_1R_{12}$, wherein the alkyl, cycloalkyl, alkenyl, alkynyl, aryl, and heteroaryl groups are optionally substituted as defined herein. In a preferred embodiment, $R_5$ is —C(=O)aryl. In some embodiments, for example, $R_5$ preferably is —C(=O)phenyl or —C(=O)phenyl wherein the phenyl ring is substituted with methyl.

In some embodiments, compounds of Formulas 1 and 2 include those wherein $R_6$, $R_7$, and $R_8$ are independently hydrogen, alkyl, cycloalkyl, alkenyl, alkynyl, aryl, heteroaryl, —C(=O)H, C(=O)alkyl, —C(=O)alkenyl, —C(=O)alkynyl, —C(=O)aryl, —C(=O)heteroaryl, wherein the alkyl, cycloalkyl, alkenyl, alkynyl, aryl, heteroaryl, C(=O)alkyl, —C(=O)alkenyl, —C(=O)alkynyl, —C(=O)aryl, and —C(=O)heteroaryl groups are optionally substituted as defined herein or $R_7$ and $R_8$ are taken together to form a carbocyclic or heterocyclic ring of 3 to 8 atoms.

In some embodiments, compounds of Formulas 1 and 2 include those wherein $R_9$, $R_{10}$, $R_{11}$, $R_{12}$, $R_{13}$ are independently hydrogen, alkyl, cycloalkyl, alkenyl, alkynyl, aryl, heteroaryl, wherein the alkyl, cycloalkyl, alkenyl, alkynyl, aryl, and heteroaryl groups are optionally substituted as defined herein or $R_{11}$ and $R_{12}$ are taken together to form a carbocyclic or heterocyclic ring of 3 to 8 atoms.

Preferred compounds of Formulas 1 and 2 include those wherein $R_1$ is aralkyl or alkyl; $R_2$ and $R_3$ are taken together to form a carbocyclic ring of from 3 to 8 atoms; $R_4$ is $(CH_2)_m NR^9 R^{10}$, or $(CH_2)_m C(=O)NR^9R^{10}$; $R_5$ is —C(=O)aryl and m, n, $R^9$ and $R^{10}$ are as described.

Particularly preferred compounds of the present invention include those of Formulas 3 to 10:

Formula 3
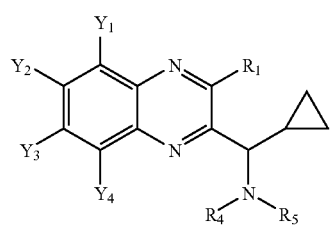

Formula 4
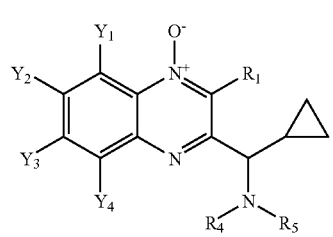

-continued

Formula 5
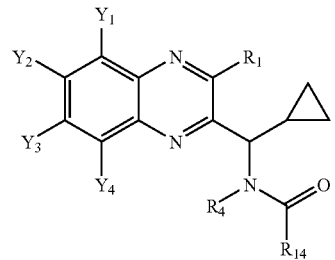

Formula 6
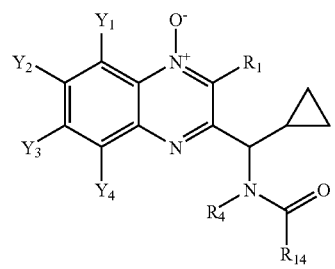

Formula 7
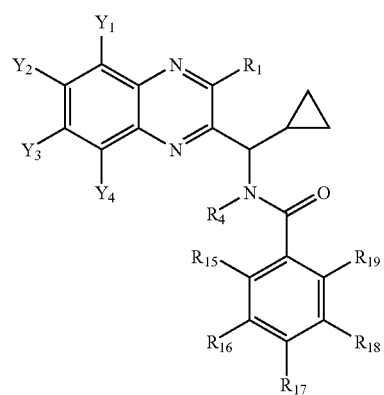

Formula 8
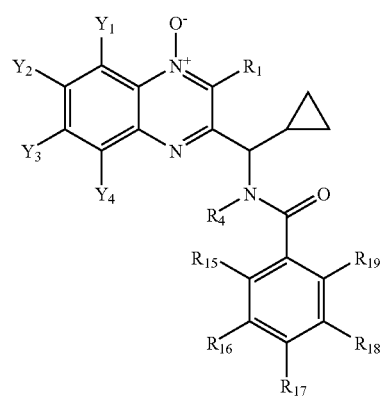

-continued

Formula 9

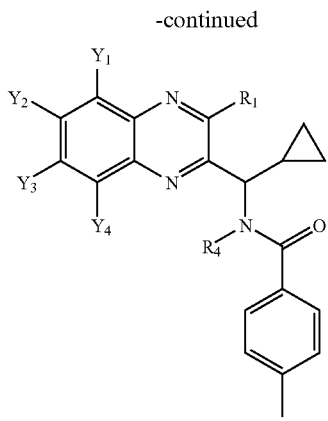

Formula 10

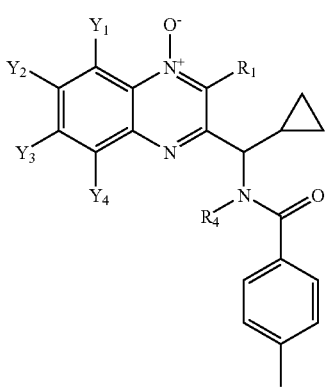

wherein
  $Y_1, Y_2, Y_3, Y_4, R_1, R_4$ and $R_5$ are as defined above for Formula 1;
  $R_{14}$ is $R_9$, $-OR_{10}$, or $NR_{11}R_{12}$ wherein $R_9, R_{10}, R_{11}$ and $R_{12}$ are as defined above for Formula 1;
  $R_{15}, R_{16}, R_{17}, R_{18}$, and $R_{19}$ are, independently hydrogen, halogen, alkyl, alkoxy, hydroxy, carboxy, carbamoyl, alkyloxycarbonyl, nitro, alkenyloxy, trifluoromethyl, amino, cycloalkyl, aryl, heteroaryl, cyano, alkyl-S(O)$_m$, or thiol; and
  m is 0, 1 or 2.

The present invention also provides, inter alia, enantiomers, diastereomers, pharmaceutically acceptable salts and esters, prodrugs and solvates of Formulas 3 to 10.

In particularly preferred embodiments of Formulas 3 to 10, $R_1$ is aralkyl or alkyl. For example in some preferred embodiments, $R_1$ is benzyl.

It is also preferred that $R_4$ be $(CH_2)_mNR^9R^{10}$, or $(CH_2)_mC(=O)NR^9R^{10}$ wherein m is 1, 2, 3, 4, or 5. For example, in some preferred embodiments, $R_4$ is $(CH_2)_mNH_2$ or $(CH_2)_mC(=O)NH_2$. In a particularly preferred embodiment, $R_4$ is $(CH_2)_3NH_2$ or $(CH_2)_3C(=O)NH_2$.

Accordingly, compounds of the present invention include those of Formulas 3 to 10 wherein $R_1$ is aralkyl or alkyl and $R_4$ is $(CH_2)_mNR^9R^{10}$ or $(CH_2)_mC(=O)NR^9R^{10}$ wherein m is from 1 to 5.

Compounds of the present invention include those of Formulas 3 to 10 wherein $R_1$ is benzyl and $R_4$ is $(CH_2)_mNH_2$ or $(CH_2)_mC(=O)NH_2$ wherein m is from 1 to 5.

In a particularly preferred embodiment of Formulas 3 to 10, $Y_1, Y_2, Y_3$ and $Y_4$ are hydrogen.

DEFINITIONS

The term "alkyl" herein alone or as part of another group refers to a monovalent alkane (hydrocarbon) derived radical containing from 1 to 12 carbon atoms unless otherwise defined. An alkyl group is an optionally substituted straight, branched or cyclic saturated hydrocarbon group. Alkyl groups can be substituted at any available point of attachment. Accordingly, the term "alkyl" includes both substituted and unsubstituted alkyl groups. An alkyl group substituted with another alkyl group is also referred to as a "branched alkyl group". Exemplary alkyl groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Exemplary substituents include but are not limited to one or more of the following groups: alkyl, aryl, halo, haloalkyl (such as $CCl_3$ or $CF_3$), alkoxy, alkylthio, hydroxy, carboxy, alkylcarbonyl, alkyloxycarbonyl, alkylcarbonyloxy, amino, carbamoyl, urea, or thiol.

The term "alkenyl" herein alone or as part of another group refers to a hydrocarbon radical straight, branched or cyclic containing from 2 to 12 carbon atoms and at least one carbon to carbon double bond. Alkenyl groups are optionally substituted at any available point of attachment. Accordingly, the term "alkenyl" includes substituted and unsubstituted alkenyl groups. Exemplary substituents for alkenyl groups include those listed above for alkyl groups.

The term "alkynyl" herein alone or as part of another group refers to a hydrocarbon radical straight, branched or cyclic containing from 2 to 12 carbon atoms and at least one carbon to carbon triple bond. Alkynyl groups are optionally substituted at any available point of attachment. Accordingly, the term "alkynyl" includes substituted and unsubstituted alkynyl groups. Exemplary substituents for alkenyl groups include those listed above for alkyl groups.

The carbon number as used in the definitions herein refers to carbon backbone and carbon branching, but does not include carbon atoms of the substituents, such as alkoxy substitutions and the like. The numbers in the subscript after the symbol "C" define the number of carbon atoms a particular group can contain. For example "$C_{1-6}$ alkyl" means a straight or branched saturated carbon chain having from one to six carbon atoms; examples include methyl, ethyl, n-propyl, isopropyl, n-butyl, sec-butyl, isobutyl, t-butyl, n-pentyl, sec-pentyl, isopentyl, and n-hexyl. Depending on the context, "$C_{1-6}$ alkyl" can also refer to $C_{1-6}$ alkylene which bridges two groups; examples include propane-1,3-diyl, butane-1,4-diyl, 2-methyl-butane-1,4-diyl, and the like. "$C_{2-6}$ alkenyl" means a straight or branched carbon chain having at least one carbon-carbon double bond, and having from two to six carbon atoms; examples include ethenyl, propenyl, isopropenyl, butenyl, isobutenyl, pentenyl, and hexenyl. Depending on the context, "$C_{2-6}$ alkenyl" can also refer to $C_{2-6}$ alkenediyl which bridges two groups; examples include ethylene-1,2-diyl (vinylene), 2-methyl-2-butene-1,4-diyl, 2-hexene-1,6-diyl, and the like. "$C_{2-6}$ alkynyl" means a straight or branched carbon chain having at least one carbon-carbon triple bond, and from two to six carbon atoms; examples include ethynyl, propynyl, butynyl, and hexynyl.

The terms "cycloalkyl" and "carbocyclic ring" are used interchangeably and herein alone or as part of another group refer to stable, saturated or partially unsaturated cyclic ring hydrocarbyls containing from 3 to 15 carbon atoms, without alternating or resonating double bonds between carbon atoms. Exemplary groups include cyclopropyl, cyclobutyl, cyclopentyl, cyclohexyl, adamantyl, and the like. The term "cycloalkyl" or "carbocyclic ring" includes substituted and unsubstituted cycloalkyl groups or carbocyclic rings. The carbocyclic ring can be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkylcarbonyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy), aryl (preferably phenyl), said aryl being optionally substituted by halo, lower alkyl and lower alkoxy groups, —$CO_2H$, —C(=O)H, $CO_2$-alkyl, —C(=O)alkyl, keto, =N—OH, =N—O-alkyl, aryl, heteroaryl, heterocyclo, a five or six membered ketal (i.e. 1,3-dioxolane or 1,3-dioxane), —NR'R", —C(=O)NR'R", —$CO_2$NR'R", —C(=O)NR'R", —NR'$CO_2$R", —NR'C(=O)R", —$SO_2$NR'R", and —NR'$SO_2$R", wherein each of R' and R" is independently selected from hydrogen, alkyl, substituted alkyl, and cycloalkyl, or R' and R" together form a heterocyclo or heteroaryl ring.

The terms "alkoxy" or "alkylthio" herein alone or as part of another group denote an alkyl group as described above bonded through an oxygen linkage (—O—) or a sulfur linkage (—S—), respectively.

The term "alkyloxycarbonyl" herein alone or as part of another group denotes an alkoxy group bonded through a carbonyl group. An alkoxycarbonyl radical is represented by the formula: —C(O)OR, where the R group is a straight or branched $C_{1-6}$ alkyl group, cycloalkyl, aryl, or heteroaryl.

The term "alkylcarbonyl" herein alone or as part of another group refers to an alkyl group bonded through a carbonyl group.

The term "aminocarbonyl" herein alone or as part of another group refers to an amino group bonded through a carbonyl group.

The term "monoalkylaminocarbonyl" herein alone or as part of another group refers to an monoalkylamino group bonded through a carbonyl group.

The term "dialkylaminocarbonyl" herein alone or as part of another group refers to dialkylamino group bonded through a carbonyl group.

The term "alkylamido" herein alone or as part of another group is represented by the formula —NHC(=O)R or —C(=O)NHR where R represents alkyl.

The term "alkylcarbonyloxy" herein alone or as part of another group denotes an alkylcarbonyl group bonded through an oxygen linkage.

The term "aralkyl" herein alone or as part of another group denotes an aromatic ring bonded through an alkyl group as described above.

The term "carboxy" herein alone or as part of another group is represented by the formula —COOH.

The term "carbamoyl" herein alone or as part of another group refers to an amino group bonded through a carboxy group.

The term "urea" as used herein is represented by the formula —NHC(=O)NHR

The term "thiol" is represented by the formula —SH.

The term "dialkylamino" as used herein refers to the group —N(Alkyl)$_2$.

The term "aryl" herein alone or as part of another group refers to monocyclic or bicyclic aromatic rings, e.g. phenyl, substituted phenyl and the like, as well as groups which are fused, e.g., napthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. Preferably, the aryl groups of the present invention have from 6 to 14 carbon atoms. The term aryl includes both substituted and unsubstituted aryl groups. Aryl groups can optionally be substituted with one or more groups including, but not limited to halogen, alkyl, alkoxy, hydroxy, carboxy, carbamoyl, alkyloxycarbonyl, nitro, alkenyloxy, trifluoromethyl, amino, cycloalkyl, aryl, heteroaryl, cyano, alkyl S(O)$_m$(m=0, 1, 2), or thiol.

The term "amino" herein alone or as part of another group refers to —$NH_2$ group that optionally is substituted with one or two substituents that are the same or different, such as alkyl, aryl, aralkyl, alkenyl, alkynyl, cycloalkyl, heteroaryl, heteroarylalkyl, heterocycloalkyl, haloalkyl, hydroxyalkyl, alkoxyalkyl, thioalkyl, carbonyl or carboxyl. These substituents can be further substituted with a carboxylic acid, or any of the alkyl or aryl substituents set out herein. In some embodiments, the amino groups are substituted with carboxyl or carbonyl to form N-acyl or N-carbamoyl derivatives.

The term "heteroaryl" herein alone or as part of another group refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups can contain only carbon atoms and can be saturated, partially saturated, or unsaturated. The nitrogen and sulfur atoms can optionally be oxidized and the nitrogen atoms can optionally be quaternized. Heteroaryl groups which are bicyclic or tricyclic must include at least one fully aromatic ring but the other fused ring or rings can be aromatic or non-aromatic. The heteroaryl group can be attached at any available nitrogen or carbon atom of any ring. The heteroaryl ring system can contain, for example, zero, one, two or three substituents selected from the group consisting of halo, alkyl, substituted alkyl, alkenyl, alkynyl, aryl, nitro, cyano, hydroxy, alkoxy, thioalkyl, —$CO_2H$, —C(=O)H, —$CO_2$-alkyl, —C(=O)alkyl, phenyl, benzyl, phenylethyl, phenyloxy, phenylthio, cycloalkyl, substituted cycloalkyl, heterocyclo, heteroaryl, —NR'R", —C(=O)NR'R", —$CO_2$NR'R", —C(=O)NR'R", —NR'$CO_2$R", —NR'C(=O)R", —$SO_2$NR'R", and —NR'$SO_2$R", wherein each of R' and R" is independently selected from hydrogen, alkyl, substituted alkyl, and cycloalkyl, or R' and R" together form a heterocyclo or heteroaryl ring.

Exemplary monocyclic heteroaryl groups include pyrrolyl, pyrazolyl, pyrazolinyl, imidazolyl, oxazolyl, diazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

The term "heterocycloalkyl" herein alone or as part of another group refers to a cycloalkyl group (nonaromatic) in which at least one of the carbon atoms in the ring is replaced by a heteroatom selected from O, S or N, and in which up to three additional carbon atoms can be replaced by said heteroatoms.

The term "heterocyclic ring" herein alone or as part of another group refers to a stable, saturated, or partially unsaturated monocyclic, bridged monocyclic, bicyclic, and spiro ring system containing 5 to 7 ring members of carbon atoms and other atoms selected from nitrogen, sulfur and/or oxygen. Preferably, a heterocyclic ring is a 5 or 6-membered monocyclic ring and contains one, two, or three heteroatoms selected from nitrogen, oxygen and/or sulfur. The heterocyclic ring can be optionally substituted which means that the heterocyclic ring can be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkylcarbonyl, —C(=O)H, aminocarbonyl, monoalkylaminocarbonyl, dialkylaminocarbonyl, alkyl amido (preferably lower alkyl amido), alkoxyalkyl (preferably a lower alkoxy [lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. Examples of such heterocyclic rings are isoxazolyl, imidazolinyl, thiazolinyl, imidazolidinyl, pyrrolyl, pyrrolinyl, pyranyl, pyrazinyl, piperidyl, morpholinyl and triazolyl. The heterocyclic ring can be attached to the parent structure through a carbon atom or through any heteroatom of the heterocyclyl that results in a stable structure.

The term "heteroatom" means O, S or N, selected on an independent basis. It should be noted that any heteroatom with unsatisfied valences is assumed to have the hydrogen atom to satisfy the valences.

The term "halogen" or "halo" refers to chlorine, bromine, fluorine or iodine selected on an independent basis.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al., *Protective Groups in Organic Synthesis*, Wiley, N.Y. (1991), herein incorporated by reference in its entirety and for all purpose.

Exemplary salt forms of the compounds herein include, but are not limited to, sodium salts and potassium salts. Other exemplary salt forms of these compounds include, but are not limited to, those formed with pharmaceutically acceptable inorganic and organic bases known in the art. Salt forms prepared using inorganic bases include hydroxides, carbonates or bicarbonates of the therapeutically acceptable alkali metals or alkaline earth metals, such as sodium, potassium, lithium, magnesium, calcium and the like. Acceptable organic bases include amines, such as benzylzmine, mono-, di- and trialkylamines, preferably those having alkyl groups of from 1 to 6 carbon atoms, more preferably 1 to 3 carbon atoms, such as methylamine, dimethylamine, trimethylamine, ethylamine, diethylamine, triethylamine, mono-, di-, and triethanolamine. Exemplary salts also include alkylene diamines containing up to 6 carbon atoms, such as hexamethylenediamine; cyclic saturated or unsaturated bases containing up to 6 carbon atoms, including pyrrolidine, piperidine, morpholine, piperazine and their N-alkyl and N-hydroxyalkyl derivatives, such as N-methyl-morpholine and N-(2-hyroxyethyl)-piperidine, or pyridine. Quaternary salts can also be formed, such as tetralkyl forms, such as tetramethyl forms, alkyl-alkanol forms, such as methyl-triethanol or trimethyl-monoethanol forms, and cyclic ammonium salt forms, such as N-methylpyridinium, N-methyl-N-(2-hydroxyethyl)-morpholinium, N,N-di-methylmorpholinium, N-methyl-N-(2-hydroxyethyl)-morpholinium, or N,N-dimethyl-piperidinium salt forms. Particularly preferred salts include hydrochloride, hydrobromide, sulfate, trifluoroacetate, methanesulfonate, maleate, fumarate, and phosphate. Salts which are unsuitable for pharmaceutical uses but which can be employed, for example, for the isolation or purification of free compounds or their pharmaceutically acceptable salts, are also included.

Certain of the compounds of Formulas 1 to 10 contain stereogenic carbon atoms or other chiral elements and thus give rise to stereoisomers, including enantiomers and diastereomers. All stereoisomers of the compounds of the instant invention are contemplated, either in admixture or in pure or substantially pure form. The definition of the compounds according to the invention embraces all possible stereoisomers and their mixtures. Throughout this application, the name of the product, where the absolute configuration of an asymmetric center is not indicated is intended to embrace the individual stereoisomers as well as mixtures of stereoisomers.

Where an enantiomer (or a particular blend of enantiomers) is preferred, it can, in some embodiments, be provided substantially free of the corresponding enantiomer(s). Thus, an enantiomer substantially free of the corresponding enantiomer refers to a compound that is isolated or separated via separation techniques or prepared free of the corresponding enantiomer. "Substantially free," as used herein, means that the compound is made up of a significantly greater proportion of one enantiomer. In preferred embodiments, the compound is made up of at least about 90% by weight of a preferred enantiomer. In other embodiments of the invention, the compound is made up of at least about 99% by weight of a preferred enantiomer. Preferred enantiomers can be isolated from racemic mixtures by any method known to those skilled in the art, including high performance liquid chromatography (HPLC) and the formation and crystallization of chiral salts, or preferred enantiomers can be prepared by methods described herein. The racemic forms can be resolved by physical methods, such as, for example, fractional crystallization, separation or crystallization of diastereomeric derivatives or separation by chiral column chromatography. The individual optical isomers can be obtained from the racemates by conventional methods, such as, for example, salt formation with an optically active acid followed by crystallization. Methods for the preparation of preferred enantiomers are described, for example, in Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, NY, 1962); and Wilen, S. H. Tables of Resolving Agents and Optical Resolutions p. 268 (E. L. Eliel, Ed., Univ. of Notre Dame Press, Notre Dame, Ind. 1972), each of which is incorporated herein by reference in its entirety and for all purposes. Accordingly, the present invention embraces the racemic forms of the claimed compounds and the isolated optical isomers having the specified activity.

It should be understood that the present invention includes prodrug forms of the compounds of Formulas 1 to 10. Various forms of prodrugs are well known in the art. For examples of such prodrug derivatives, see: (a) Design of Prodrugs, edited by H. Bundgaard (Elsevier, 1985); and Methods in Enzymology, Vol. 112, pp. 309-396, edited by K. Widder et al., (Academic Press, 1985); (b) A Textbook of Drug Design and Development, edited by Krosgaard-Larsen and H. Bundgaard, Chapter 5, "Design and Application of Prodrugs," by H. Bundgaard, pp. 113-191 (1991); (c) H. Bundgaard, Advanced Drug Deliver Reviews, 8, pp. 1-38 (1992); (d) H. Bundgaard et al., Journal of Pharmaceutical Sciences, 77, 285 (1988); and (e) N. Kayeka et al., Chem. Phar. Bull., 32, 692 (1984), each of which is incorporated herein by reference in its entirety and for all purposes.

Solvates (e.g., hydrates) of the compounds of the present invention are also within the scope of the present invention. Methods of solvation are generally known in the art. Accordingly, the compounds of the instant invention can be in the free or hydrate form, and can be obtained by methods exemplified by the following schemes below.

Compounds of the present invention can be prepared by those skilled in the art of organic synthesis employing conventional methods that utilize readily available reagents and starting materials. Representative compounds of the present invention can be prepared using the following synthetic schemes. The skilled practitioner will know how to make use of variants of these process steps.

Intermediate 3 can be prepared from the starting material 2,3-dichloroquinoxaline 1 following the reaction in Scheme 1. In this manner, quinoxaline 1 can be reacted with benzylmagnesium chloride in THF to afford 2-benzyl-3-chloroquinoxaline 2. 2-Benzylquinoxalines can also be prepared by reaction with alternative alkylating reagents, such as, but not limited to, benzyllithium. 2-Benzyl-3-chloroquinoxaline 2 can be reacted with cyanide to obtain intermediate 2-benzyl-3-cyanoquinoxaline 3.

SCHEME 1

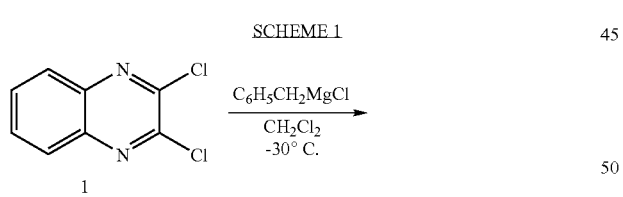

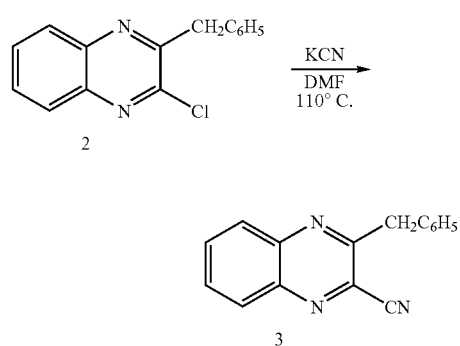

Cyclopropyl methylamine side chain can be introduced by reacting cyanoquinoxaline 3 with cyclopropylmagnesium bromide followed by the reduction of the resulting imine intermediate 4 in situ after adjusting the pH of the reaction mixture to 4~6 as shown in Scheme 2 to afford racemic cyclopropylmethylamine substituted quinoxaline 5.

SCHEME 2

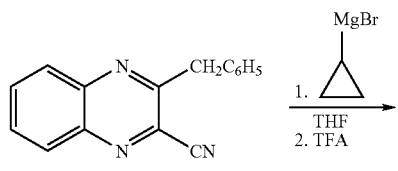

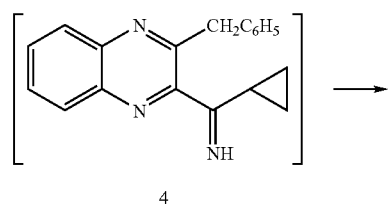

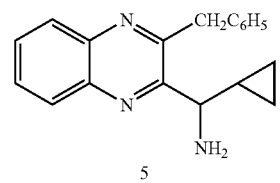

Aminoalkyl side chain can be introduced via reductive alkylation such as with N-Boc-aminopropanal using NaBH(OAc)$_3$ to obtain N-Boc protected amine 6 as shown in Scheme 3. Acylation of the amine 6 with the proper acylhalides such as p-toluolchloride in the presence of base can provide the compounds with the amide side chain such as 7. Deprotection of the Boc-group of quinoxaline 7 or quinoxaline N-oxide 9 which can be obtained by the oxidation using mCPBA can afford the final product such as quinoxalin analog 8 or quinoxaline N-oxide analog 10, respectively.

SCHEME 3
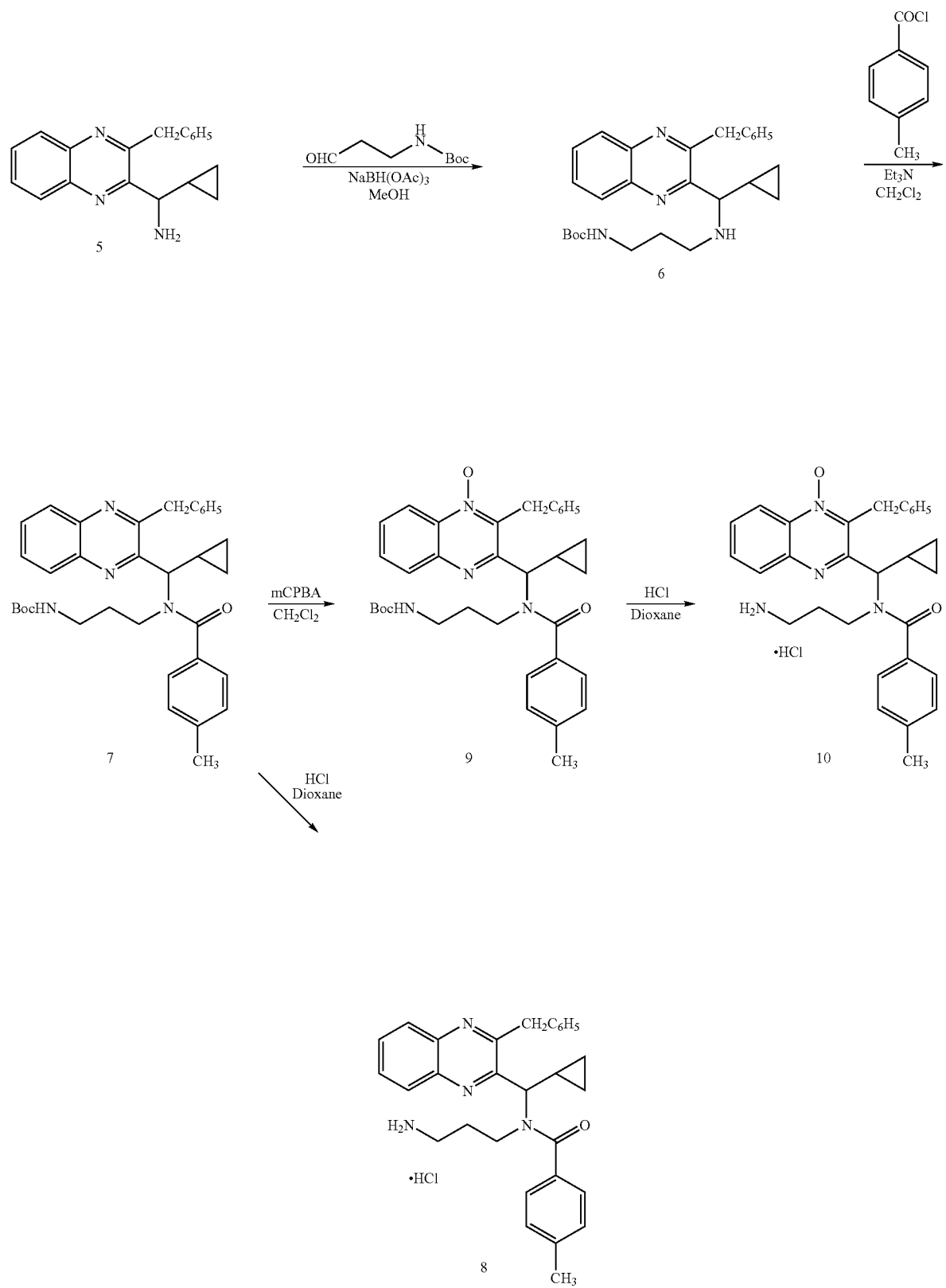

Halogen substituted in ring A quinoxaline analogs such as chlorine can be obtained starting from chloroquinoxaline 11 (prepared generally following the literature procedure, Heterocycles, 1985, 23, 143-151, herein incorporated by reference). Cyanation of 11 followed by bromination using bromination agent such as POBr₃ provides quinoxaline 13 (scheme 4). Alkyl or arylalkyl can be introduced to C-3 via Pd-mediated coupling reaction using such as benzyl-tri-n-butyl tin agent 14 to afford 3-benzylquinoxaline 15.

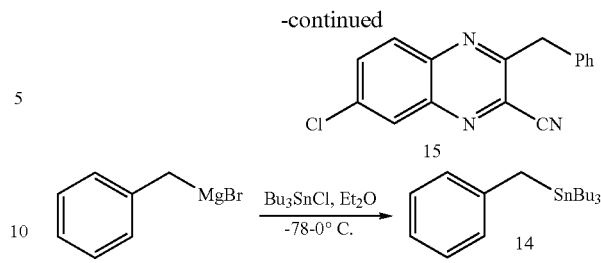

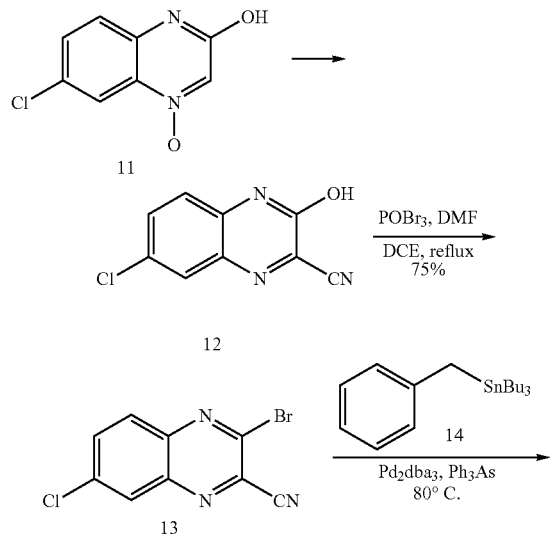

Alkyl or aryl substituted quinoxaline amine can be obtained by reacting cyanoquinoxaline 15 with alkyl or aryl magnesiumhalides such as cyclopropyl magnesiumbromide followed by reduction of the resulting imine intermediate with sodium triacetoxyborohydride to produce 16 (Scheme 5). Alkylation of the amino side chain can be achieved via reductive alkylation using substituted alkylaldehydes such as N-Boc-aminopropanal in the presence of reducing reagent to provide 17.

Acylation using various alkyl or aryl acylhalides followed by deprotection of the Boc-group with the acid affords the quinoxaline analog 19 as a HCl amine salt. Oxidation of the quinoxaline 18 using oxidizing agent such as mCPBA provides quinoxaline N-oxide 20 and deprotection of the boc-group with acid affords the quinoxaline N-oxide analog 21 as a HCl amine salt.

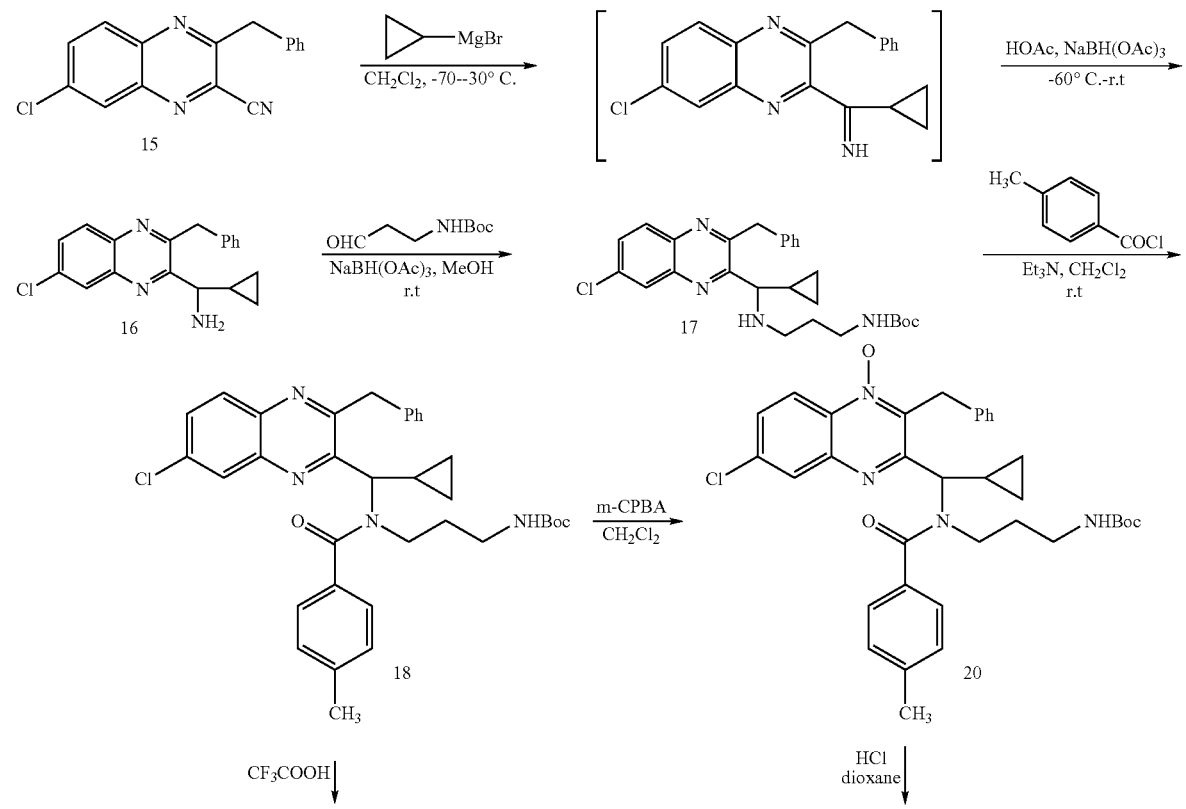

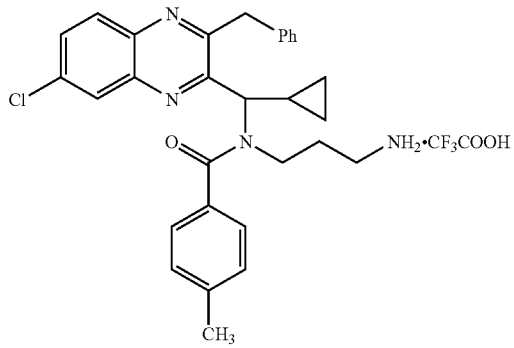

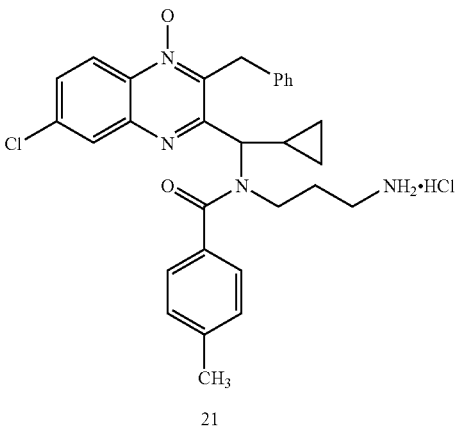

Analogues containing the 3-aminopropanoic acid derivative side chain can be prepared from intermediate 16 via Michael addition followed by acylation, hydrolysis and amide formation using ammonium carbonate as shown in Scheme 6.

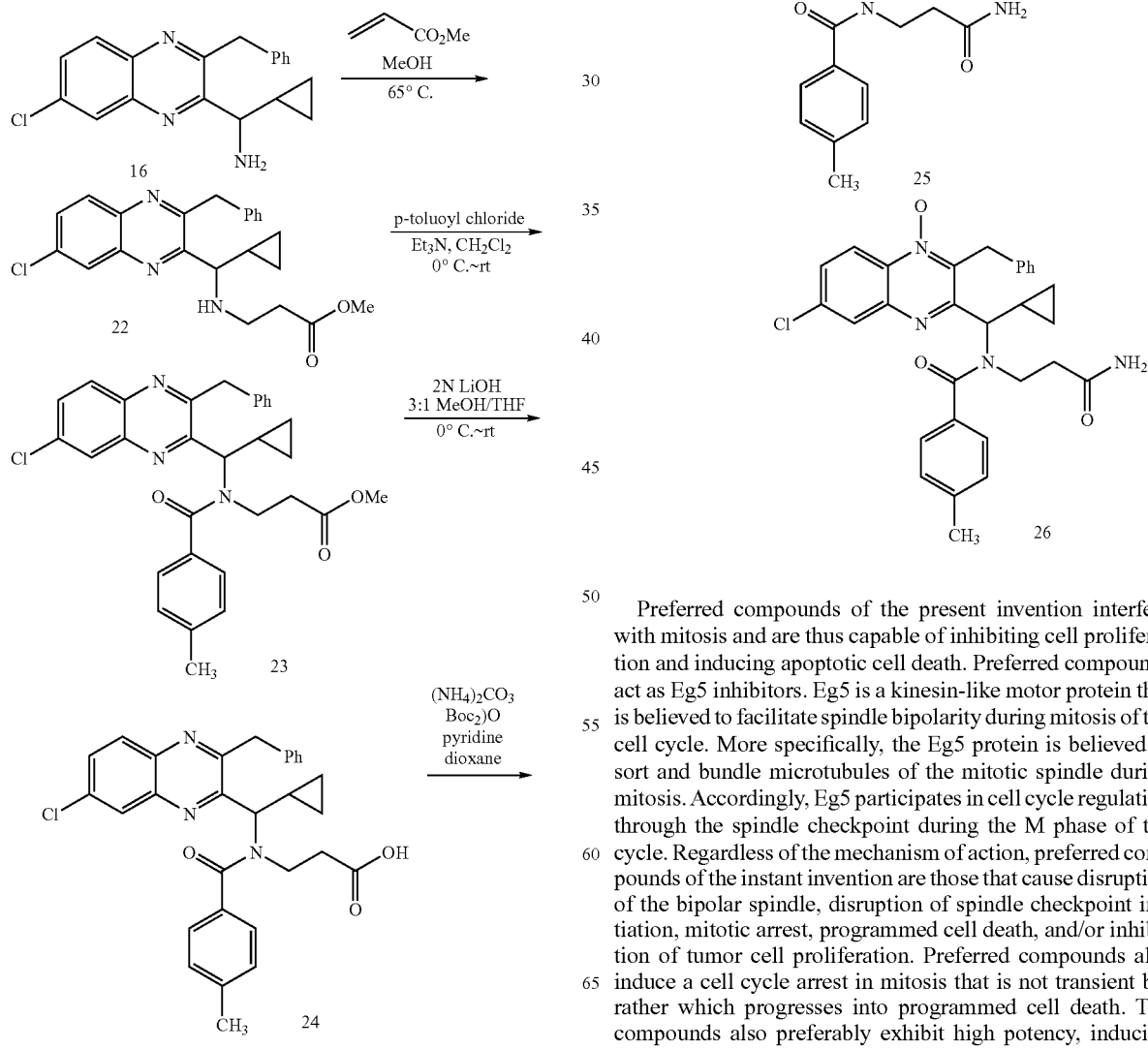

Preferred compounds of the present invention interfere with mitosis and are thus capable of inhibiting cell proliferation and inducing apoptotic cell death. Preferred compounds act as Eg5 inhibitors. Eg5 is a kinesin-like motor protein that is believed to facilitate spindle bipolarity during mitosis of the cell cycle. More specifically, the Eg5 protein is believed to sort and bundle microtubules of the mitotic spindle during mitosis. Accordingly, Eg5 participates in cell cycle regulation through the spindle checkpoint during the M phase of the cycle. Regardless of the mechanism of action, preferred compounds of the instant invention are those that cause disruption of the bipolar spindle, disruption of spindle checkpoint initiation, mitotic arrest, programmed cell death, and/or inhibition of tumor cell proliferation. Preferred compounds also induce a cell cycle arrest in mitosis that is not transient but rather which progresses into programmed cell death. The compounds also preferably exhibit high potency, inducing mitotic arrest and apoptosis in human cells in vitro at concentrations in the low or sub µM range. One can therefore more specifically target the mitotic spindle of proliferating cells, which can provide for different toxicity profiles than those of existing anti-cancer drugs.

It is also preferred that compounds of the instant invention inhibit other motor proteins including, but not limited to, those human motor proteins that correspond to, Xklp2, MKLP1, CHO1, chromokinesins, Nod, Cenp-E, MCAK, members of the BimC family, and members of the Kar3 family. Additionally, preferred compounds used in the methods of the instant invention can also act as inhibitors of other kinesin or kinesin-like proteins and thus be effective in the treatment of diseases associated with other kinesin or kinesin-like proteins.

The present invention provides methods for treating proliferative diseases (e.g., via modulation of the Eg5 motor protein), and/or inducing apoptosis comprising administering to a mammalian species in need of such treatment an effective amount of a compound of Formulas 1 to 10 as defined above. In another embodiment, the invention provides methods for treating proliferative diseases comprising administering to a mammalian species in need of such treatment an effective amount of a compound of Formula 1 to 10 as defined above, in combination (simultaneously or sequentially) with at least one other anti-cancer or anti-proliferative agent. In a preferred embodiment, the proliferative disease is cancer.

The compounds according to the invention have pharmacological properties that can be confirmed by a number of pharmacological assays, including but not limited to 72 hour proliferation assay, clonogenic growth assay, immunocytochemistry assays. Preferably, the compounds of the present invention induce mitotic arrest, and are thus useful in the therapy of a variety of proliferative diseases (including, but not limited to, diseases associated with the Eg5 motor protein) such as cancer, autoimmune diseases, viral diseases, fungal diseases, neurodegenerative disorders and cardiovascular disease.

The term "cancer" refers to any of a number of diseases characterized by uncontrolled, abnormal proliferation of cells; the ability of affected cells to spread locally or through the bloodstream and lymphatic system to other parts of the body (i.e., metastasize); as well as any of a number of characteristic structural and/or molecular features.

Proliferative diseases are those characterized by proliferating cells, i.e., those actively undergoing cell division and growing exponentially. Such cells can also be viewed as having lost cell proliferation control, i.e., lost the cell cycle controls that normally ensure appropriate restriction of cell division. Cells that have lost such controls proliferate at a faster than normal rate, without stimulatory signals, and do not respond to inhibitory signals.

Preferred compounds of the present invention are useful in the treatment of a variety of cancers, including, but not limited to, carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma; hematopoietic tumors of lymphoid lineage, including leukemia, acute lymphocytic leukemia, acute lymphoblastic leukemia, B-cell lymphoma, T-cell lymphoma, Hodgkin's lymphoma, non-Hodgkins lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma. The methods of the present invention can be used, for example, to arrest tumor growth, inhibit tumor growth or cause tumor regression. In some embodiments, the tumors will be malignant tumors, e.g., malignant liposarcomas and epithelial tumors. In other embodiments, the tumors will be benign, such as adenomas. Accordingly, diseases caused by benign tumors, e.g., acromegaly, are also treatable by the methods of the present invention.

Due to the key role of motor proteins in the regulation of cellular proliferation in general, inhibitors of motor proteins, such as the compounds disclosed herein, can act as reversible cytostatic agents which can be useful in the treatment of any disease process which features abnormal cellular proliferation, e.g., benign prostatic hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

Preferred compounds of the invention induce apoptosis. The apoptotic response is aberrant in a variety of human diseases. Compounds that modulate apoptosis are useful in the treatment of cancer (including but not limited to those types mentioned herein above), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

Compounds of the present invention preferably modulate the level of cellular RNA and DNA synthesis. These agents are useful in the treatment of viral infections (including but not limited to HIV, human papilloma virus, herpesvirus, poxvirus, Epstein-Barr virus, Sindbis virus and adenovirus).

Compounds of the present invention preferably are useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse. Preferred compounds of the present invention can be used for the inhibition of tumor angiogenesis and metastasis.

The compounds of the present invention can be administered to a subject for a variety of purposes. Except when noted, the terms "subject" or "patient" are used interchangeably and refers to all mammalian species. For example, the term includes mammals such as human patients and non-human primates, as well as experimental animals such as rabbits, rats, and mice, and other animals. Accordingly, the term "subject" or "patient" as used herein means any mammalian patient or subject to which the compounds of the invention can be administered. Patients for treatment according to the methods of the invention preferably are identified using accepted screening methods to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and formulations of the present invention. A subject "in need thereof" is a subject suffering or suspected to be suffering from a certain condition or disease state treatable by the methods of the present invention.

As used herein, the term "treating" or "treatment" refers to any indicia of success in amelioration of an injury, pathology, or condition, including any objective or subjective parameter such as abatement; remission; diminishing of symptoms or making the injury, pathology, or condition more tolerable to the patient; slowing in the rate of degeneration or decline; making the final point of degeneration less debilitating; or improving a subject's physical or mental well-being. The treatment or amelioration of symptoms can be based on objective or subjective parameters; including the results of a physical examination, neurological examination, and/or psychiatric evaluation. "Treating" or "treatment of a cell proliferative disorder" includes preventing the onset of symptoms in a subject that may be predisposed to a cell proliferative disease but does not yet experience or exhibit symptoms of the disorder (prophylactic treatment), inhibiting the symptoms of the disorder (slowing or arresting its development), providing relief from the symptoms or side-effects of the disorder (including palliative treatment), and/or relieving the symptoms of the disorder (causing regression). Accordingly, the term "treating" includes the administration of the compounds or agents of the present invention to a subject to prevent or delay, to alleviate, or to arrest or inhibit development of the symptoms or conditions associated with cell proliferative disease, e.g., tumor growth associated with cancer. A skilled medical practitioner will know how to use standard methods to determine whether a patient is suffering from a disease associated with abnormal cell proliferation.

"Concomitant administration" of a known drug or treatment with a pharmaceutical composition of the present invention means administration of the drug (or treatment) and the quinoxaline compound at such time that both the known drug (or treatment) and the composition of the present invention will have a therapeutic effect. Such concomitant administration can involve concurrent (i.e. at the same time), prior, or subsequent administration of the drug (or treatment) with respect to the administration of a compound of the present invention. A person of ordinary skill in the art, would have no difficulty determining the appropriate timing, sequence and dosages of administration for particular drugs and compositions of the present invention. For example, the compounds of this invention can be used in combination (administered together or sequentially) with known anti-cancer treatments such as radiation therapy or with cytostatic or cytotoxic agents, such as for example, but not limited to, DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones, either naturally occurring or synthetic; hormonal agents, such as tamoxifen; thymidilate synthase inhibitors, such as 5-fluorouracil, and UFT; and anti-metabolites, such as methotrexate, tyrosine kinase inhibitors such as Iressa and OSI-774; angiogenesis inhibitors; EGF inhibitors; VEGF inhibitors; CDK inhibitors; SRC inhibitors; c-Kit inhibitors; Her1/2 inhibitors and monoclonal antibodies directed against growth factor receptors such as erbitux (EGF) and herceptin (Her2).

The present invention provides compositions comprising a compound of the present invention in combination with a pharmaceutically acceptable carrier. In a preferred embodiment, the quinoxaline compounds are formulated as pharmaceuticals to diseases associated with abnormal cell proliferation.

In general, quinoxaline compounds can be administered as pharmaceutical compositions by any method known in the art for administering therapeutic drugs including oral, buccal, topical, systemic (e.g., transdermal, intranasal, or by suppository), or parenteral (e.g., intramuscular, subcutaneous, or intravenous injection). Compositions can take the form of tablets, pills, capsules, semisolids, powders, sustained release formulations, solutions, suspensions, emulsions, syrups, elixirs, aerosols, or any other appropriate compositions; and can comprise at least one compound of this invention in combination with at least one pharmaceutically acceptable excipient. Suitable excipients are well known to persons of ordinary skill in the art, and they, and the methods of formulating the compositions, can be found in such standard references as Alfonso A R: Remington's Pharmaceutical Sciences, 17th ed., Mack Publishing Company, Easton Pa., 1985, incorporated herein by reference in its entirety and for all purposes. Suitable liquid carriers, especially for injectable solutions, include water, aqueous saline solution, aqueous dextrose solution, and glycols. In some embodiments of the present invention, compound suitable for use in the practice of this invention can also be administered with at least one other conventional therapeutic agent for the disease being treated.

The pharmaceutical compositions containing the active ingredient can be in a form suitable for oral use, for example, as tablets, troches, lozenges, aqueous or oily suspensions, dispersible powders or granules, emulsions, hard or soft capsules, or syrups or elixirs. Compositions intended for oral use can be prepared according to any method known to the art for the manufacture of pharmaceutical compositions and such compositions can contain one or more agents selected from the group consisting of, for example, sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients can be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets can be uncoated or they can be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate buryrate can be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents can be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example, ethyl, or n-propyl p-hydroxybenzoate, one or more coloring agents, one or more flavoring agents, and one or more sweetening agents, such as sucrose, saccharin or aspartame.

Oily suspensions can be formulated by suspending the active ingredient in a vegetable oil, for example arachis oil, olive oil, sesame oil or coconut oil, or in mineral oil such as liquid paraffin. The oily suspensions can contain a thickening agent, for example beeswax, hard paraffin or cetyl alcohol. Sweetening agents such as those set forth above, and flavoring agents can be added to provide a palatable oral preparation. These compositions can be preserved, for example, by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, can also be present. These compositions can be preserved by the addition of an anti-oxidant such as ascorbic acid.

The pharmaceutical compositions of the invention can also be in the form of an oil-in-water emulsions. The oily phase can be a vegetable oil, for example olive oil or arachis oil, or a mineral oil, for example liquid paraffin or mixtures of these. Suitable emulsifying agents can be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions can also contain sweetening, flavoring agents, preservatives and antioxidants.

Syrups and elixirs can be formulated with sweetening agents, for example glycerol, propylene glycol, sorbitol or sucrose. Such formulations can also contain, for example, a demulcent, a preservative, flavoring and coloring agents and antioxidant.

The pharmaceutical compositions can be in the form of a sterile injectable aqueous solutions. Among the acceptable vehicles and solvents that can be employed, for example, are water, Ringer's solution and isotonic sodium chloride solution.

The sterile injectable preparation can also be a sterile injectable oil-in-water microemulsion where the active ingredient is dissolved in the oily phase. For example, the active ingredient can be first dissolved in a mixture of soybean oil and lecithin. The oil solution then introduced into a water and glycerol mixture and processed to form a microemulation.

The injectable solutions or microemulsions can be introduced into a patient's blood-stream by local bolus injection. Alternatively, it can be advantageous to administer the solution or microemulsion in such a way as to maintain a constant circulating concentration of the instant compound. In order to maintain such a constant concentration, a continuous intravenous delivery device can be utilized. An example of such a device is the Deltec CADD-PLUS™ model 5400 intravenous pump.

The pharmaceutical compositions of the present invention can be in the form of a sterile injectable aqueous or oleagenous suspension for intramuscular and subcutaneous administration. This suspension can be formulated according to the known art using those suitable dispersing or wetting agents and suspending agents which have been mentioned above. The sterile injectable preparation can also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

Compounds of the present invention can also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include, for example, cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, and the like containing the compounds of Formulas 1 to 10 can be employed. For purposes of this application, topical application include mouth washes and gargles.

The compounds of the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will be continuous rather than intermittent throughout the dosage regimen. Compounds of the present invention can also be delivered as a suppository employing bases such as cocoa butter, glycerinated gelatin, hydrogenated vegetable oils, mixtures of polyethylene glycols of various molecular weights and fatty acid esters of polyethylene glycol.

Encapsulating materials can also be employed with the compounds of the present invention and the term "composition" is intended to include the active ingredient in combination with an encapsulating material as a formulation, with or without other carriers. For example, the compounds of the present invention can also be delivered as microspheres for slow release in the body. In one embodiment, microspheres can be administered via intradermal injection of drug (e.g., mifepristone)-containing microspheres, which slowly release subcutaneously (see Rao, J. Biomater Sci. Polym. Ed. 7:623-645, 1995; as biodegradable and injectable gel formulations (see, e.g., Gao, Pharm. Res. 12:857-863, 1995); or, as microspheres for oral administration (see, e.g., Eyles, J. Pharm. Pharmacol. 49:669-674, 1997). Both transdermal and intradermal routes afford constant delivery for weeks or months.

A pharmaceutical composition of the invention can optionally contain, in addition to a quinoxaline compound, at least one other therapeutic agent useful in the treatment of a disease or condition associated with abnormal cell proliferation.

The pharmaceutical compositions are generally formulated as sterile, substantially isotonic and in full compliance with all Good Manufacturing Practice (GMP) regulations of the U.S. Food and Drug Administration.

For treatment purposes, the compositions or compounds disclosed herein can be administered to the subject in a single bolus delivery, via continuous delivery (e.g., continuous transdermal, mucosal, or intravenous delivery) over an extended time period, or in a repeated administration protocol (e.g., by an hourly, daily or weekly, repeated administration protocol).

In this context, a therapeutically effective dosage or pharmaceutically effective dosage of the biologically active agent(s) can include repeated doses within a prolonged treatment regimen that will yield clinically significant results to alleviate one or more symptoms or detectable conditions associated with, for example, proliferative diseases. Determination of effective dosages in this context is typically based on animal model studies followed up by human clinical trials and is guided by determining effective dosages and administration protocols that significantly reduce the occurrence or severity of targeted exposure symptoms or conditions in the subject. Suitable models in this regard include, for example, murine, rat, non-human primate, and other accepted animal model subjects known in the art. The actual dosage of biologically active agents will of course vary according to factors such as the type of disease and particular status of the subject (e.g., the subject's age, size, fitness, extent of symptoms, susceptibility factors, and the like), time and route of administration, as well as other drugs or treatments being administered concurrently. Dosage regimens can be adjusted to provide an optimum prophylactic or therapeutic response. By "therapeutically effective dose" or "pharmaceutically effective dose" herein is meant a dose that produces effects for which it is administered. More specifically, a therapeutically effective dose or pharmaceutically effective dose of the compound(s) of the invention, for example, preferably alleviates symptoms, complications, or biochemical indicia of diseases or disorders associated with abnormal cell proliferation. The exact dose will depend on the purpose of the treatment, and will be ascertainable by one skilled in the art using known techniques (see, e.g., Lieberman, Pharmaceutical Dosage Forms (Vols. 1-3, 1992); Lloyd, 1999, The Art, Science, and Technology of Pharmaceutical Compounding; and Pickar, 1999, Dosage Calculations). A therapeutically effective dose is also one in which any toxic or detrimental side effects of the active agent is outweighed in clinical terms by therapeutically beneficial effects. It is to be further noted that for each particular subject, specific dosage regimens should be evaluated and adjusted over time according to the individual need and professional judgment of the person administering or supervising the administration of the compound.

In an exemplary embodiment of the present invention, unit dosage forms of the compounds are prepared for standard administration regimens. In this way, the composition can be subdivided readily into smaller doses at the physicians direction. For example, unit dosages can be made up in packeted powders, vials or ampoules and preferably in capsule or tablet form.

After a pharmaceutical comprising a substituted a quinoxaline compound has been formulated in a suitable carrier, it can be placed in an appropriate container and labeled for treatment of a proliferative disease, e.g., cancer. Additionally, another pharmaceutical comprising at least one other therapeutic agent useful in the treatment of such diseases can be placed in the container as well and labeled for treatment of the indicated disease. Alternatively, a single pharmaceutical comprising an quinoxaline compound and at least one other therapeutic agent can be placed in an appropriate container and labeled for treatment. For administration of pharmaceuticals comprising quinoxaline compounds and of pharmaceuticals comprising, in a single pharmaceutical, quinoxaline compounds and at least one other therapeutic agent useful in the treatment of proliferative disease, such labeling would include, for example, instructions concerning the amount, frequency and method of administration. Similarly, for administration of multiple pharmaceuticals provided in the container, such labeling would include, for example, instructions concerning the amount, frequency and method of administration of each pharmaceutical.

EXAMPLES

The following examples and preparations describe the manner and process of making and using the invention and are illustrative rather than limiting. It should be understood that there can be other embodiments which fall within the spirit and scope of the invention as defined by the claims appended hereto.

Examples 1 through 4 demonstrate the synthesis of representative compounds of the present invention. All temperatures are in degrees Celsius (° C.) unless otherwise indicated. Preparative Reverse Phase (RP) HPLC purifications were carried out on C18 reverse phase (RP) columns using water/methanol mixtures with 0.1% TFA as buffer solution. The following abbreviations are used for the commonly used reagents: BOC: t-butyl carbamate, FMOC: 9H-fluorenylmethyl carbamate, NMM: N-methylmorpholine, NMP: N-methylpyrrolidinone, BOP reagent: benzotriazol-1-yloxytris (trimethylamino)phosphonium hexafluorophosphate, EDCI: 1-(dimethylaminopropyl)-3-ethylcarbodiimide hydrochloride, rt: room temperature, PyBOP: bromotripyrrolidinophosphonium hexafluorophosphate, HOBt: hydroxybenzotriazole, $NaBH(OAc)_3$: sodium triacetoxyborohydride, $Pd_2dba_3$: Tris(dibenzylideneacetone)dipalladium(0), HOAc: acetic acid, HCl: hydrochloric acid, TFA: trifluoroacetic acid, KHMDS: potassium bis(trimethylsilyl)amide, DMSO: dimethyl sulfoxide, MeCN: acetonitrile, MeOH: methanol, EtOAc: ethyl acetate, DMF: dimethyl formamide, THF: tetrahydrofuran. All LC/MS data were obtained using the following conditions: YMC S5 ODS 4.6×50 mm column, eluting with 10-90% aqueous methanol containing 0.1% TFA, using a gradient of 4 minutes with a 4 mL/min flow rate, monitoring at 220 nm. The $^1H$ NMR spectra were obtained on a 400 or 500 MHz Bruker or Jeol instrument, respectively. The $^{13}C$ NMR spectra were recorded at 100 or 125 MHz. Unless otherwise noted, all reagents were purchased from Aldrich.

Example 11 provides assays that were performed with representative compounds of the present invention. The representative compounds exhibited antiproliferative activity.

Example 1

Synthesis of (±)-N-(3-Amino-propyl)-N-[(3-benzyl-quinoxalin-2-yl)-cyclopropyl-methyl]-4-methylbenzamide hydrochloride

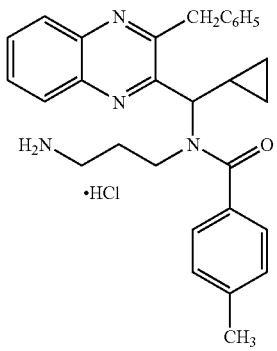

(A) 2-Benzyl-3-chloro-quinoxaline (2): To a suspension of 2,3-dichloroquinoxaline 1 (19 g, 91.6 mmol, commercially available) in anhydrous $CH_2Cl_2$ (150 mL) at −36° C. under nitrogen was added dropwise benzylmagnesium chloride (2 M, 100 mL, 200 mmol) in THF over 1 hr. The reaction mixture was stirred at −30° C. for 30 min and was added additional benzylmagnesium chloride (10 mL, 20 mmol). The reaction was quenched with aq. $NH_4Cl$ and 1N HCl, and diluted with EtOAc to 200 mL. The organic layer was separated and the aq. layer was extracted with EtOAc (3×100 mL). The combined organic solution was dried over $MgSO_4$ and concentrated. Purification by flash column (SiO$_2$, EtOAc/hexane 1:100 to 1:50) gave 2 as a light brown solid (9.15 g, 39%). $^1$H NMR (CDCl$_3$) δ 8.02 (m, 1H), 7.91 (m, 1H), 7.69 (m, 2H), 7.28 (m, 2H), 7.21 (m, 2H), 7.18 (m, 1H), 4.44 (s, 2H); $^{13}$C NMR (CDCl$_3$) δ 154.1, 147.6, 140.9, 136.3, 130.3, 130.1, 129.2, 128.9, 128.5, 128.3, 128.1, 126.8, 42.0; MS (ESI), (M+H)$^+$255.03, 257.02.

(B) 2-Benzyl-3-cyano-quinoxaline (3): A mixture of 2-benzyl-3-chloroquinoxaline 2 (8.0 g, 31.4 mmol) and potassium cyanide (2.50 g, 38.4 mmol) in anhydrous DMF (100 mL) was heated at 100-115° C. under nitrogen for 8.5 hr. It was diluted with EtOAc to 500 mL, washed with 10% aq. LiCl three times and dried over $MgSO_4$. Concentration and purification by flash column (SiO$_2$, EtOAc/hexane 5:95) gave 3 as a pinkish solid (4.56 g, 60%). $^1$H NMR (CDCl$_3$) δ 8.06 (m, 2H), 7.84 (m, 1H), 7.76 (m, 1H), 7.38 (d, 2H, J=7.65 Hz), 7.25 (m, 2H), 7.19 (m, 2H); $^{13}$C NMR (CDCl$_3$) δ 156.3, 142.4, 140.6, 136.3, 133.2, 130.9, 130.1, 129.6, 129.2, 128.8, 127.2, 115.9, 41.9; MS (ESI), (M+H)$^+$246.

(C) (±)-C-(3-Benzyl-quinoxalin-2-yl)-C-cyclopropyl-methylamine (5): To a stirred solution of 2-benzyl-3-cyanoquinoxaline 3 (4.1 g, 16.8 mmol) in anhydrous $CH_2Cl_2$ (150 mL) at −73° C. under nitrogen was added dropwise cyclopropyl-magnesium bromide (0.76 M, 67 mL, 51 mmol) in THF over 25 min. The reaction mixture was warmed to −30° C. and stirred for for 50 min. at −30° C., then was cooled to −68° C., TFA (12 mL) was added dropwise to the mixture followed by NaBH(OAc)$_3$ (12 g, 20 mmole). It was slowly warmed to r.t over 6 hr, and additional 1.6 g of NaBH(OAc)$_3$ was added and stirred overnight. The reaction was quenched with aq. NaHCO$_3$, and was extracted with EtOAc (2×200 mL). The organic solution was dried over $MgSO_4$ and concentrated. Purification by flash column (SiO$_2$, EtOAc/hexane MeOH/NH$_4$OH 30:70:3:0.3 to 60:40:6:0.5) gave 5 as an oil (1.0 g, 20%). $^1$H NMR (CDCl$_3$) δ 8.12 (m, 2H), 7.77 (m, 2H), 7.31 (m, 2H), 7.24 (m, 3H), 4.58 (s, 2H), 3.85 (d, 1H, J=8.25 Hz), 1.43 (m, 1H), 0.55 (m, 1H), 0.35 (m, 1H), 0.23 (m, 1H), 0.01 (m, 1H); $^{13}$C NMR (CDCl$_3$) δ 153.2, 150.5, 141.7, 140.1, 137.2, 130.3, 129.8, 128.9, 128.8, 128.7, 128.6, 126.9, 54.5, 41.1, 15.0, 3.82, 2.04; MS (ESI), (M+H)$^+$290.16.

(D) (±)-(3-{[(3-Benzyl-quinoxalin-2-yl)-cyclopropyl-methyl]-amino}-propyl)-carbamic acid tert-butyl ester (6): To a stirred solution of (±)-C-(3-benzyl-quinoxalin-2-yl)-cyclopropyl-methylamine, 5 (1.10 g, 3.8 mmol) in MeOH (20 mL) at rt under nitrogen was added N-Boc-amino-propanal (3.6 g, 20.8 mmole). The reaction mixture was stirred for 20 min, then treated with HOAc (0.3 mL) followed by NaBH(OAc)$_3$ (2.7 g, 12.1 mmol) for 2 hr. It was quenched with aq. NaHCO$_3$, and extracted with EtOAc (3×80 mL). The organic solution was dried over $MgSO_4$ and concentrated. Purification by flash column (SiO$_2$, EtOAc/hexane MeOH/NH$_4$OH 30:70:3:0.3 to 50:50:5:0.5) gave 6 as a light brown oil (1.36 g, 80%). $^1$H NMR (CDCl$_3$) δ 7.24 (m, 2H), 7.19 (m, 1H), 7.09 (m, 2H), 7.00 (d, 1H, J=4.4 Hz), 6.44 (d, 1H, J=4.4 Hz), 5.33 (q, 2H, AB), 4.10 (t 1H, J=7.15 Hz), 2.62 (d, 1H, J=7.7 Hz), 1.40 (m, 1H), 0.51 (m, 2H), 0.32 (m, 1H), 0.14 (m, 1H); $^{13}$C NMR (CDCl$_3$) δ 154.3, 150.5, 136.1, 129.0, 127.8, 126.2, 117.8, 117.3, 110.2, 108.6, 72.76, 44.6, 15.5, 3.0; MS (ESI), (M+H)$^+$447.33.

(E) (±)-{3-[[(3-Benzylquinoxalin-2-yl)cyclopropylmethyl]-(4-methylbenzoyl)-amino]-propyl}carbamic acid tert-butyl ester (7): To a stirred solution of (±)-(3-{[(3-benzylquinoxalin-2-yl)cyclopropylmethyl]-amino}-propyl)carbamic acid tert-butyl ester, 6 (1.10 g, 2.46 mmol) and Et$_3$N (0.50 mL, 3.59 mmole) in $CH_2Cl_2$ (20 mL) at rt under nitrogen was added p-toluoyl chloride (0.41 mL, 3.1 mmol). The reaction mixture was stirred for 50 minutes. It was diluted with EtOAc to 100 mL, washed with aq. NaHCO$_3$ (30 mL) and brine (30 mL). The organic solution was dried over $MgSO_4$ and concentrated. Purification by flash column chromatography (SiO$_2$, EtOAc/hexane 1:9 to 1:3) gave 7 as a light brown oil (0.82 g, 59%). $^1$H NMR (CDCl$_3$) δ 8.06 (m, 1H), 8.01 (m, 1H), 7.69 (m, 2H), 7.18 (m, 9H), 5.47 (m, 1H), 4.63 (d, 2H, J=14.85 Hz), 4.31 (d 1H, J=14.85 Hz), 3.50 (m, 1H), 3.40 (m, 1H), 2.52 (m, 2H), 2.24 (s, 3H), 1.96 (m, 1H), 1.57 (m, 1H), 1.35 (m, 1H), 1.25 (s, 9H), 0.95 (m, 1H), 0.49 (m, 1H), 0.41 (m, 1H), 0.21 (m, 1H); $^{13}$C NMR (CDCl$_3$) δ 174.7, 157.7, 155.9, 154.9, 141.8, 141.7, 140.5, 139.2, 134.6, 130.5, 129.9, 129.6, 129.3, 129.0, 127.5, 127.0, 79.4, 60.1, 43.9, 41.3, 38.3, 31.9, 28.4, 21.1, 13.9, 5.14, 4.21; MS (ESI), (M+H)$^+$565.39.

(F) (±)-N-(3-Amino-propyl)-N-[(3-benzyl-quinoxalin-2-yl)-cyclopropyl-methyl]-4-methylbenzamide hydrochloride (8):

A solution of (±)-{3-[[(3-benzylquinoxalin-2-yl)cyclopropylmethyl]-(4-methyl-benzoyl)-amino]-propyl}carbamic acid tert-butyl ester 7 (0.40 g, 0.71 mmol) in dioxane (5 mL) at rt was added 4 N HCl in dioxane (2.0 mL, 8 mmol). The reaction mixture was stirred overnight. It was added with Et$_2$O and the precipitated solid was collected, washed with Et$_2$O and dried in vacuo over P$_2$O$_5$ to give 8 (0.32 g, 90%). $^1$H NMR (CD$_3$OD) δ 8.15 (m, 2H), 7.87 (m, 2), 7.36 (m, 4H), 7.22 (m, 5H), 6.56 (m, 1H), 5.52 (m, 1H), 4.75 (m, 1H), 4.23 (m, 1H), 3.69 (m, 2H), 3.65 (s, 3H), 3.06 (m, 1H), 2.39 (m, 4H), 2.10 (m, 1H), 1.98 (m, 1H), 1.85 (m, 1H), 1.46 (m, 1H), 0.63 (m, 2H), 0.46 (m, 1H), 0.29 (m, 2H); $^{13}$C NMR (CD$_3$OD) δ 155.5, 142.3, 141.2, 135.2, 131.9, 130.5, 130.1, 130.0, 129.8, 129.6, 128.0, 127.3, 68.5, 43.2, 41.8, 38.9, 30.5, 21.7, 14.4, 5.78; MS (ESI), (M+H)⁺465.31.

Example 2

Synthesis of (±)-N-(3-Aminopropyl)-N-[(3-benzyl-4-oxyquinoxalin-2-yl)cyclopropylmethyl]-4-methylbenzamide hydrochloride

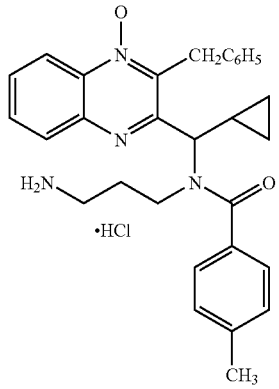

(A) (±)-{3-[[(3-Benzyl-4-oxyquinoxalin-2-yl)cyclopropylmethyl]-(4-methylbenzoyl)-amino]-propyl}carbamic acid tert-butyl ester (9): To a stirred solution of (±)-{3-[[(3-benzylquinoxalin-2-yl)cyclopropylmethyl]-(4-methylbenzoyl)amino]propyl}carbamic acid tert-butyl ester 7 (0.30 g, 0.53 mmol) in $CH_2Cl_2$ (16 mL) at rt was added m-chloroperbenzoic acid (0.25 g, 0.1 mmol). The reaction mixture was stirred overnight. It was added a few drops of DMSO and stirred for 5 minutes. The reaction mixture was diluted with $CH_2Cl_2$ to 80 mL, washed with aq. $NaHCO_3$ (2×25 mL). The $CH_2Cl_2$ solution was dried over $MgSO_4$ and concentrated to give 9 as a light yellow foam (0.29 g, 94%). $^1H$ NMR ($CDCl_3$) δ 8.56 (m, 1H), 8.06 (d, 1H, J=8.25 Hz), 7.70 (m, 2H), 7.09 (m, 9H), 5.40 (m, 1H), 4.98 (m, 1H), 4.50 (m, 1H), 3.50 (m, 2H), 2.69 (m, 1H), 2.28 (s, 3H), 1.79 (m, 2H), 1.31 (s, 9H), 1.10 (m, 1H), 0.51 (m, 2H), 0.32 (m, 1H), −0.40 (m, 1H); %). MS (ESI), (M+H)⁺581.35.

(B) (±)-N-(3-Aminopropyl)-N-[(3-benzyl-4-oxyquinoxalin-2-yl)cyclopropylmethyl]-4-methylbenzamide hydrochloride (10): A solution of (±)-{3-[[(3-benzyl-4-oxyquinoxalin-2-yl)cyclopropylmethyl]-(4-methylbenzoyl)amino]-propyl}carbamic acid tert-butyl ester 9 (0.50 g, 0.86 mmol) in dioxane (5 mL) at rt was added 4 N HCl in dioxane (2.5 mL, 10 mmol). The reaction mixture was stirred overnight. It was added with $Et_2O$ and the precipitated solid was collected, washed with $Et_2O$ and dried in vacuo over $P_2O_5$ to give 10 as a HCl salt (0.37 g, 83.4%). $^1H$ NMR ($D_2O$) δ 8.56 (m, 1H), 8.06 (d, 1H, J=8.25 Hz), 7.70 (m, 2H), 7.09 (m, 9H), 5.40 (m, 1H), 4.98 (m, 1H), 4.50 (m, 1H), 3.50 (m, 2H), 2.69 (m, 1H), 2.28 (s, 3H), 1.79 (m, 2H), 1.31 (s, 9H), 1.10 (m, 1H), 0.51 (m, 2H), 0.32 (m, 1H), −0.40 (m, 1H); $^{13}C$ NMR ($D_2O$) δ 174.6, 157.5, 156.0, 143.2, 141.2, 135.5, 132.1, 129.7, 129.5, 129.0, 127.6, 127.4, 126.2, 118.4, 61.2, 42.9, 37.9, 37.1, 32.1, 28.3, 27.2, 20.7, 12.9, 5.70, 3.96; MS (ESI), (M+H)⁺481.27.

Example 3

Synthesis of (±)-N-(3-Aminopropyl)-N-[(3-benzyl-7-chloroquinoxalin-2-yl)cyclopropyl-methyl]-4-methylbenzamide hydrochloride

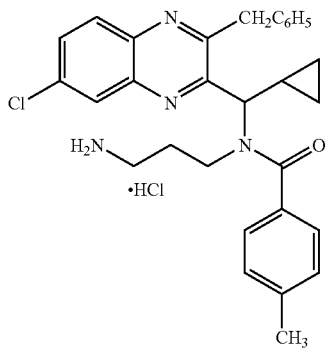

(A) 7-Chloro-3-hydroxy-quinoxaline-2-carbonitrile (12): A mixture of N-oxide 11 (14 g, 71.2 mmol) and trimethylsilylcyanide (25 g, 252.0 mmol) was heated at 100~115° C. for 3 hrs. To the reaction mixture aq NaHCO₃ (160 mL) and EtOAc (400 mL) were added, stirred for 10 min. and the precipitated solid was filtered. This solid was a mixture of undesired product as a major and a starting material and desired product 12. The organic solution was separated, washed with water (100 mL), and the aqueous solution was extracted with EtOAc (3×400 mL), the combined organic solution was dried over MgSO₄, concentrated in vacuo to obtain desired product 12 (7.8 g) as a solid. This solid was slightly contaminated by impurities, but it was used directly for the next step without any further purification.

$^1H$ NMR (DMSO-d₆) δ 7.97 (d, 1H, J=2.2 Hz), 7.75 (dd, 1H, J₁=8.8 Hz, J₂=2.2 Hz), 7.35 (d, 1H, J=8.8 Hz); $^{13}C$ NMR (DMSO-d₆) δ 141.4, 140.5, 138.3, 15.4, 132.5, 130.6, 129.8, 128.5114.6; MS (ESI), (M+H)⁺206.18, 208.17.

(B) 3-Bromo-7-chloroquinoxaline-2-carbonitrile (13): A mixture of 6-chloro-4-oxy-quinoxalin-2-ol, 12 (11.8 g, 57.4 mmol), POBr₃ (29 g, 101 mmol) and DMF (0.2 mL) in 1,2-dichloroethane (140 mL) was heated at reflux under nitrogen for 9 h. The reaction mixture was cooled to 0° C. and quenched with diluted aq. NaOH solution. After stirred for 30 min, the precipitated solid was collected, washed with water, and dried over P₂O₅ in vacuum to give 13 (13.7 g, 88%). $^1H$ NMR (CDCl₃) δ 8.08 (d, 1H, J=2.2 Hz), 8.0 (d, J=8.8 Hz, 1H), 7.84 (dd, 1H, J₁=8.8 Hz, J₂=2.2 Hz); $^{13}C$ NMR (CDCl₃) δ 153.2, 136.9, 134.1, 132.4, 132.3, 128.7, 128.3, 118.1, 114.8; MS (ESI), (M+H)⁺269.26.

(C) 3-Benzyl-7-chloro-quinoxaline-2-carbonitrile (15): To a stirred solution of 3-bromo-7-chloro-quinoxaline-2-carbonitrile 13 (0.65 g, 24.3 mmol) under Ar atm. in DMF (0.2 mL) was added with Pd₂dba₃ (1.09 g, 1.18 mmol) and Ph₃As (1.46 g, 4.77 mmol) and the mixture was stirred at rt for a few minutes and then was added with benzyltributyltin (14.0 g, 36.6 mmole). The reaction mixture was heated at 80° C. for 2 h, cooled to rt and the insoluble material was filtered. The filtrate solution was diluted with EtOAc to 250 mL, washed with aq. 10% LiCl solution (3×80 mL) and brine (100 mL). The organic solution was dried over MgSO₄ and concentrated. The product was crystallized from Et₂O/Hexane and the solid was filtered and dried to give 15 (4.07 g, 60%).

Purification of the residue from the mother liquid by flash column (SiO$_2$, EtOAc/hexane 5:95) provided additional 15 as light yellow solid (2.12 g, 31%). $^1$H NMR (CDCl$_3$) δ 8.04 (m, 2H), 7.78 (m, 1H), 7.36 (m, 2H), 7.25 (m, 2H), 7.18 (m, 1H), 4.49 (s, 2H); $^{13}$C NMR (CDCl$_3$) δ 156.5, 140.9, 140.8, 137.1, 136.0, 134.2, 130.9, 130.4, 129.2, 128.8, 128.3, 127.3, 115.6, 41.8; MS (ESI), (M+H)$^+$280.25.

(D) Benzyl-tributyl-stannane (14): To a stirred solution of tributyltin chloride (10.0 mL, 36.8 mmol) in Et$_2$O (100 mL) at −40° C. under nitrogen was added butylmagnesiumchloride (1.0 M, 37 mL, 37 mmol). The reaction mixture was stirred at −40° C. to rt for 1 h, then passed through a thick layer of silica gel, washed with Et$_2$O. The filtrate was concentrated to give 14 as a colorless oil (14.2 g, 100%).

$^1$H NMR (CDCl$_3$) δ 7.08 (m, 2H), 6.90 (m, 3H), 2.22 (s, 2H), 1.40 (m, 6H), 1.26 (m, 12H), 0.86 (m, 9H).

(E) (±)-(3-Benzyl-7-chloroquinoxalin-2-yl)-cyclopropyl-methylamine (16): To a stirred solution of 3-benzyl-7-chloro-2-cyanoquinoxaline (4.0 g, 14.3 mmol) in anhydrous CH$_2$Cl$_2$ (80 mL) at −64° C. under nitrogen was added dropwise cyclopropylmagnesium bromide (0.76 M in THF, 52 mL, 39.5 mmol). The reaction mixture was stirred at −68~−30° C. for 40 min. It was cooled to −60° C. and TFA (12 mL) was added to the reaction mixture followed by NaBCNH$_3$ (1.25 g, 18.9 mmol). The mixture was slowly warmed to −20° C. over 20 min, and then cooled to −30° C. and quenched with aq. NaHCO$_3$ and extracted with CH$_2$Cl$_2$ (2×100 mL). The organic solution was washed with brine (60 mL), dried over MgSO$_4$ and concentrated. Purification by flash column (SiO$_2$, EtOAc/hexane MeOH/NH$_4$OH 30:70:3:0.3) gave C-(3-Benzyl-7-chloro-quinoxalin-2-yl)-cyclopropyl-methylamine (16) as an oil (1.8 g). This oily product was slightly contaminated by impurities, but it was used directly for the next step without any further purification. $^1$H NMR (CDCl$_3$) δ 8.02 (m, 1H), 7.96 (m, 1H), 7.67 (m, 1H), 7.19 (m, 5H), 4.52 (m, 1H), 4.41 (m, 2H), 1.37 (m, 1H), 0.61 (m, 1H), 0.36 (m, 1H), 0.12 (m, 1H), 0.01 (m, 1H); MS (ESI), (M+H)$^+$323.26, 325.26.

(F) (±)-(3-{[(3-Benzyl-7-chloroquinoxalin-2-yl)-cyclopropyl-methyl]-amino}-propyl)-carbamic acid tert-butyl ester (17): To a stirred solution of crude product 16 obtained above in MeOH (10 mL) at rt under nitrogen was added N-Boc-aminopropanal (3.0 g, 17.3 mmol). The reaction mixture was stirred for 20 min, and then was treated with HOAc (0.25 mL) followed by NaBH(OAc)$_3$ (1.25 g, 5.6 mmol). Additional NaBH(OAc)$_3$ (8.75 g, 39.2 mmole) and N-Boc-amino-propanal (1.0 g, 5.8 mmole) were added as the reaction proceeded. It was quenched with aq. NaHCO$_3$, and extracted with EtOAc (3×80 mL). The organic solution was dried over MgSO$_4$ and concentrated. Purification by flash column (SiO$_2$, EtOAc/hexane MeOH/NH$_4$OH 30:70:3:0.3 to 50:50:5:0.5) gave 17 as a light brown oil (1.35 g, 20%). $^1$H NMR (CDCl$_3$) δ 8.06 (m, 1H), 8.01 (d, 1H, J=8.8 Hz, 7.65 (m, 1H), 7.26 (m, 2H), 7.20 (m, 1H), 7.15 (d, 2H, J=7.15 Hz), 5.19 (m, 1H), 4.44 (s, 2H), 3.68 (d, 1H, J=7.7 Hz), 3.00 (m, 2H), 2.19 (m, 1H, 2.11 (m, 1H), 1.44 (m, 13H), 1.20 (m, 1H), 0.51 (m, 1H), 0.26 (m, 1H), 0.12 (m, 1H), 0.01 (m, 1H); $^3$C NMR (CDCl$_3$) δ 158.4, 155.9, 154.6, 141.6, 139.6, 137.8, 135.0, 130.3, 130.0, 128.8, 128.7, 127.8, 126.9, 78.8, 61.8, 45.5, 41.8, 39.4, 29.5, 28.4, 16.2, 3.68, 1.25; MS (ESI), (M+H)$^+$481.32, 483.33.

(G) (±)-{3-[[(3-Benzyl-7-chloroquinoxalin-2-yl)cyclopropylmethyl]-(4-methylbenzoyl)amino]-propyl}carbamic acid tert-butyl ester (18): To a stirred solution of (±)-(3-{[(3-benzyl-7-chloroquinoxalin-2-yl)cyclopropyl-methyl]-amino}propyl)carbamic acid tert-butyl ester, 17 (1.10 g, 2.46 mmol) and Et$_3$N (0.50 mL, 3.59 mmol) in CH$_2$Cl$_2$ (15 mL) at rt under nitrogen was added p-toluoyl chloride (0.38 mL, 3.1 mmol). The reaction mixture was stirred for 30 min. It was diluted with CH$_2$Cl$_2$ to 60 mL, washed with aq. NaHCO$_3$ (2×30 mL), 10% aq. citric acid (30 mL) and brine (30 mL). The CH$_2$Cl$_2$ solution was dried over MgSO$_4$ and concentrated to give 18 as a brown oil (1.30 g, 94%). $^1$H NMR (CDCl$_3$) δ 8.09 (m, 2H), 7.72 (m, 1H), 7.26 (m, 4H), 7.19 (m, 5H), 6.56 (m, 1H), 5.48 (d, 1H, J=9.45 Hz), 4.75 (d, 1H, J=14.85 Hz), 4.41 (d, 1H, J=14.85 Hz), 3.55 (m, 1H), 2.72 (m, 2H), 2.40 (m, 1H), 2.35 (s, 3H), 1.85 (m, 1H), 1.60 (m, 1H), 1.39 (s, 9H), 0.49 (m, 2H), 0.24 (m, 1H); $^{13}$C NMR (CDCl$_3$) δ 173.1, 159.3, 158.9, 155.4, 155.2, 141.1, 139.4, 137.8, 135.4, 132.8, 131.2, 129.8, 129.2, 129.0, 128.6, 127.9, 126.8, 126.2, 59.0, 42.6, 40.8, 37.8, 30.9, 28.3, 13.2, 4.81, 4.02; MS (ESI), (M+H)$^+$599.39.

(H) (±)-N-(3-Aminopropyl)-N-[(3-benzyl-7-chloroquinoxalin-2-yl)cyclopropyl-methyl]-4-methylbenzamide trifluoroacetic acid (19): A mixture of 18 (20 mg, 0.033 mmol) and TFA (0.2 mL) in CH$_2$Cl$_2$ (0.3 mL) was allowed to stay at rt for 30 min. It was concentrated and the residue was purified by preparative HPLC to give 19 as an off-white solid (18.7 mg, 91%). $^1$H NMR (DMSO-d$_6$) δ 8.21 (m, 1H), 8.13 (m, 1H), 7.90 (m, 1H), 7.55 (m, 2H), 7.20 (m, 7H), 5.40 (m, 1H), 4.60 (m, 1H), 4.36 (m, 1H), 3.45 (m, 1H), 2.40 (m, 2H), 2.35 (s, 3H), 1.90 (m, 2H), 1.60 (m, 1H), 0.65 (m, 1H), 0.45 (m, 1H), 0.30 (m, 1H), 0.40 (m, 1H); MS (ESI), (M+H)$^+$499.20, 501.20.

Example 4

Synthesis of (±)-N-(3-Aminopropyl)-N-[(3-benzyl-7-chloro-4-oxyquinoxalin-2-yl)cyclopropyl-methyl]-4-methylbenzamide hydrochloride (21)

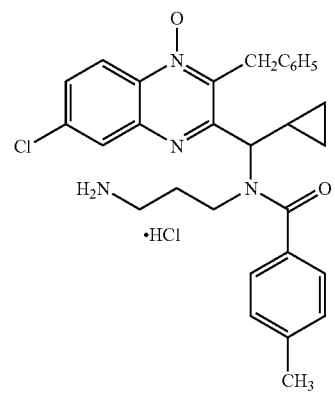

(A) (±)-{3-[[(3-Benzyl-7-chloro-4-oxyquinoxalin-2-yl) cyclopropylmethyl]-(4-methylbenzoyl)-amino]-propyl}carbamic acid tert-butyl ester (20): To a stirred solution of (±)-{3-[[(3-benzyl-7-chloroquinoxalin-2-yl)-cyclopropyl-methyl]-(4-methylbenzoyl)amino] propyl}carbamic acid tert-butyl ester, 18 (1.25 g, 2.09 mmol) in CH$_2$Cl$_2$ (15 mL) at r.t was added m-chloroperbenzoic acid (1.50 g, 6.07 mmol). The reaction mixture was stirred overnight. Additional mCPBA was added (0.9 g, 3.65 mmol) and the reaction mixture was stirred at r.t over night. It was added a few drops of DMSO and stirred for 5 minute. The reaction mixture was diluted with EtOAc to 200 mL, washed with aq. NaHCO$_3$ (3×50 mL), dried over MgSO$_4$. Concentration and purification by flash column chromatography (SiO$_2$, EtOAc/hexane 1.5:8.5 to 1:3) to give 20 as a white solid (0.78 g, 61%). $^1$H NMR (CDCl$_3$) δ 8.57 (d, 1H, J=8.8 Hz), 8.14 (d, 1H, J=2.2 Hz), 7.67 (1H, AB), 7.20 (m, 6H), 7.14 (m, 2H), 7.08 (m, 2H), 5.43 (d, 1H, J=8.8 Hz), 5.01 (d, 1H, J=14.85 Hz), 4.48 (d, 1H, J=14.3 Hz), 4.05 (m, 1H), 3.58 (m, 1H), 3.50 (m, 1H), 2.78 (m, 2H), 2.35 (s, 3H), 1.92 (m, 1H), 1.68 (m, 1H), 1.55 (m, 2H), 1.39 (s, 9H), 1.23 (m, 1H), 0.57 (m, 2H), 0.38 (m, 1H), −0.33 (m, 1H); $^{13}$C NMR (CDCl$_3$) δ 172.6, 158.1, 143.5, 139.5, 137.2, 136.8, 134.7, 132.8, 130.9, 129.1, 128.7, 128.3, 126.8, 126.3, 120.9, 59.5, 42.7, 37.9, 31.2, 28.3, 21.3, 13.2, 5.35, 4.06; MS (ESI), (M+H)$^+$ 615.24, 617.23.

(B) (±)-N-(3-Aminopropyl)-N-[(3-benzyl-7-chloro-4-oxyquinoxalin-2-yl)cyclopropyl-methyl]-4-methylbenzamide hydrochloride (21): A solution of (±)-{3-[[(3-benzyl-7-chloro-4-oxyquinoxalin-2-yl)cyclopropylmethyl]-(4-methylbenzoyl)amino]propyl}carbamic acid tert-butyl ester 20 (0.77 g, 1.25 mmol) in dioxane (5 mL) at rt was added 4 N HCl in dioxane (4 mL, 16 mmol). The reaction mixture was stirred overnight. Et$_2$O was added to the mixture and the precipitated solid was collected, washed with Et$_2$O and dissolved in H$_2$O and lyophilized to give 20 as pale solid (0.63 g, 91%). $^1$H NMR (CD$_3$OD) δ 8.56 (m, 1H), 8.24 (s, 1H), 7.84 (m, 1H), 7.25 (m, 5H), 7.11 (m, 2H), 6.80 (m, 1H), 5.40 (m, 1H), 5.01 (m, 2H), 4.50 (m, 1H), 4.65 (m, 2H), 3.15 (m, 1H), 2.55 (m, 1H), 2.40 (m, 3H), 2.00 (m, 2H), 1.60 (m, 1H), 0.70 (m, 2H), 0.55 (m, 1H), 0.45 (m, 1H), −0.25 (m, 1H); MS (ESI), (M+H)$^+$ 515.20, 517.20.

Examples 5 to 10

Examples 5 to 10 were prepared according to the general Schemes described above and generally according to the same methods outlined in examples 1 to 4.

| Example No. |  |
|---|---|
| 5 | 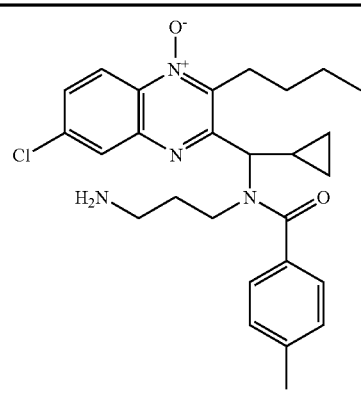 |
| 6 | 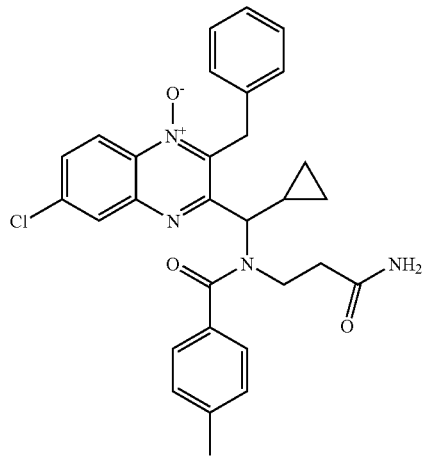 |
| 7 | 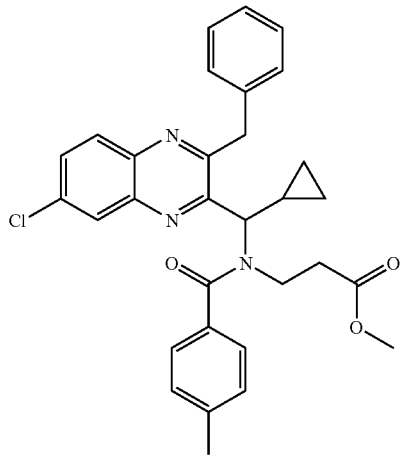 |
| 8 | 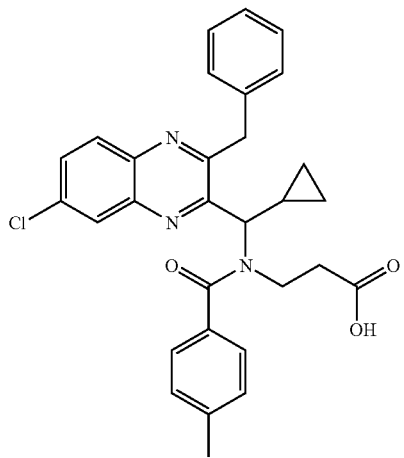 |

-continued

| Example No. | |
|---|---|
| 9 | 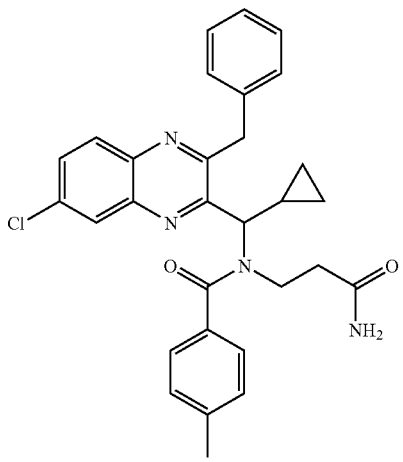 |
| 10 | 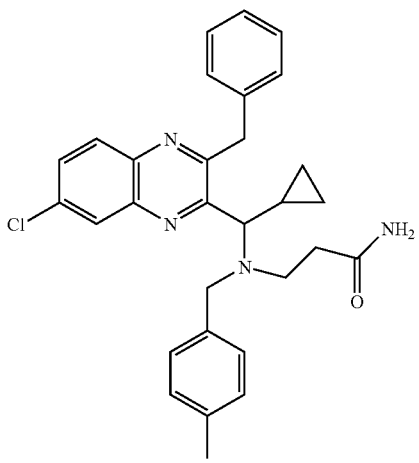 |

Example 11

The pharmacological properties of the compounds of this invention can be confirmed by a number of pharmacological assays. The exemplified pharmacological assays which follow have been carried out with the compounds according to the invention and their salts. Representative compounds of the present invention exhibited antiproliferative activity.

Cell Culture

Cell lines are maintained in RPMI-1640 plus 10% fetal bovine serum.

72-Hour Proliferation Assay

Cells were plated at a density of 3,000-6,000 cells/well, depending upon the cell line used, in a 96-well plate. The cultures were grown overnight. Cells were then treated in triplicate with a seven concentration dose-response curve. The maximum concentration of DMSO never exceeded 0.5%. Cells were exposed to compound for 72 hours. Proliferation was measured using XTT or MTS from Promega. The ovarian, breast, prostate, lung, leukemia, and colorectal human cancer cell lines used in this assay included but were not limited to, for example, A2780S, SKBR3, MDA-MB-231, PC3, LX-1, K562, HT-29, WiDr, HCT-15 and HCT116. Representative compounds of the present invention exhibited activity in the 72-hour cell proliferation assay, inhibiting cell proliferation in one or more of the cell lines listed above with at an $IC_{50}$ less than or equal to about 10 μM.

Clonogenic Growth Assay

Colony growth inhibition was measured for A2780 ovarian carcinoma cells using a standard clonogenic assay. Briefly, 200 cells/well were seeded into 6-well tissue culture plates (Falcon, Franklin Lakes, N.J.) and allowed to attach for 18 hours. Assay medium consisted of RPMI-1640 plus 10% fetal bovine serum. Cells were then treated in duplicate with a six concentration dose-response curve. The maximum concentration of DMSO never exceeded 0.25%. Cells were exposed to compound for 4, 8 or 24 hours. Compound was then removed and the cells were washed with 2 volumes of PBS. The normal growth medium was then replaced. Colonies were fed with fresh media every third day. Colony number was scored on day 10-14 using a Optimax imaging station. The compound concentration required to inhibit 50% or 90% of colony formation ($IC_{50}$ or $IC_{90}$, respectively) was determined by non-linear regression analysis. The coefficient of variance (SD/mean, n=3)=30%. When exposed to cells for 24 hours, the representative compounds exhibited activity in the clonogenecity assay.

Cell Cycle Analysis

The cell cycle profile of cells treated with representative compounds of the present invention was monitored by flow cytometry. Briefly, A2780 ovarian carcinoma cells were seeded at a density of $2\times10^5$ per well in standard 6 well culture plates and permitted to grow for 17 hours. Cells were then exposed to compounds of representative compounds at varying concentrations for 2 to 24 hours. Following exposure, cell populations were harvested, stained with propidium iodide to determine DNA content and also stained with the appropriate immunological reagent for protein biomarkers of mitosis and apoptosis, including, for example, anti-phospho-ThreonineProline, anti-M Phase Phosphoprotein 2 (MMP2), and anti-p85 PARP. The representative compounds exhibited activity in the cell cycle profile analysis assay, producing significant increases in mitotic and apoptotic fractions of the cell population.

Immunocytochemistry Assays

A2780 ovarian carcinoma cells or PTK2 kangaroo rat kidney epithelial cells were plated at a density of 200 to 2000 cells per well in 4 chamber glass slides and allowed to attach overnight. Cells were then treated with representative compounds of the present invention at concentrations of 100 nM to 50 μM for 4 to 30 hours, fixed and permeabilized for subsequent staining. Stain reagents included, for example, propidium iodide, DAPI, rhodamine phalloidin, anti-αtubulin, anti-βtubulin, anti-γtubulin, and the appropriate fluorescent-tagged secondary antibodies. Cells were imaged by fluorescent and confocal fluorescent microscropy. The representative compounds inhibited bipolar spindle formation and induced a monoastral array of microtubules.

Further subject matter of the invention also includes pharmaceuticals for use as described above including controlling cancer, inflammation and arthritis, which contain at least one compound of Formulas 1 to 10 as defined above or at least one of its pharmacologically acceptable acid addition salts, and the use of a compound of the Formulas 1 to 10 as defined above for the preparation of a pharmaceutical having activity against proliferative diseases as described previously including against cancer, inflammation and/or arthritis.

All publications and patent documents cited above are hereby incorporated by reference in their entirety for all purposes to the same extent as if each were so individually denoted.

What is claimed:

1. A compound of Formula 1 or Formula 2:

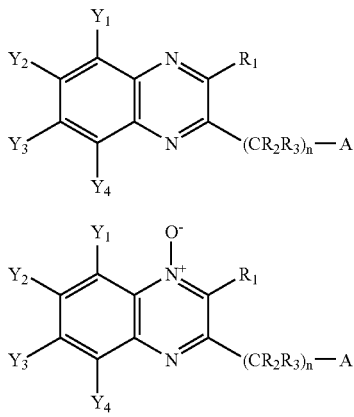

or a pharmaceutically acceptable salt or ester form thereof, wherein:
- $Y_1$, $Y_2$, and $Y_4$ are hydrogen;
- $Y_3$ is hydrogen or halogen;
- $R_1$ is alkyl or benzyl;
- $R_2$ and $R_3$ are independently hydrogen, halogen, alkyl, cycloalkyl, alkenyl, alkynyl, aryl, or heteroaryl, or $R_2$ and $R_3$ are taken together to form a carbocyclic or heterocyclic ring of 3 to 8 atoms;
- n is from 1 to 4;
- A is $O(R_4)$, $S(R_4)$ or $N(R_4)(R_5)$;
- $R_4$ is $(CH_2)_m NR_9 R_{10}$, $(CH_2)_m C(=O)NR_9 R_{10}$, or $(CH_2)_m C(=O)OR_{20}$;
- $R_5$ is $C(=O)R_9$, $C(=O)OR_{10}$, $C(=O)NR_{11}R_{12}$, $SO_2 R_9$, or $SO_2 NR_{11}R_{12}$;
- m is from 1 to 5;
- $R_9$, $R_{10}$, $R_{11}$, and $R_{12}$ are independently hydrogen, alkyl, cycloalkyl, alkenyl, alkynyl, aryl, or heteroaryl, or $R_{11}$ and $R_{12}$ are taken together to form a carbocyclic or heterocyclic ring of 3 to 8 atoms; and
- $R_{20}$ is hydrogen or alkyl;

wherein:
- "alkyl" refers to a monovalent alkane (hydrocarbon) derived radical containing from 1 to 12 carbon atoms; and where an alkyl includes both substituted and unsubstituted alkyl groups wherein the substituents may be selected from alkyl, aryl, halo haloalkyl, alkoxy, alkylthio, hydroxy, carboxy, alkylcarbonyl, alkyloxycarbonyl, alkylcarbonyloxy, amino, carbamoyl, urea, and thiol;
- "aklenyl" refers to hydrocarbon radical straight, branched or cyclic containing from 2 to 12 carbon atoms and at least one carbon to carbon double bond;
- "alkynyl" refers to a hydrocarbon radical straight, branched or cyclic containing from 2 to 12 carbon atoms and at least one carbon to carbon triple bond;
- "cycloalkyl" refers to saturated or partially unsaturated cyclic hydrocarbon rings containing from 3 to 15 carbon atoms, wherein the carbocyclic ring can be substituted at one or more substitutable ring positions by one or more groups independently selected from alkyl, alkoxy, nitro, monoalkylamino, dialkylamino, cyano, halo, haloalkyl, alkylcarbonyl, aminocarbonyl, monoalkylaminocarbonyl, dialkylaminocarbonyl, alkyl amido, alkoxyalkyl, alkoxycarbonyl, alkylcarbonlyoxy, aryl, $-CO_2 H$, $-C(=O)H$, $CO_2$-alkyl, $-C(=O)$alkyl, keto, $=N-OH$, $=N-O$-alkyl, aryl, heteroaryl, heterocyclo, a five or six membered ketal, $-NR'R''$, $-C(=O)NR'R''$, $-C(=O)NR'R''$, $-NR'CO_2R''$, $-NR'C(=O)R''$, $-SO_2 NR'R''$, and $-NR'SO_2R''$, wherein each of R' and R" is independently selected from hydrogen, alkyl, or R' and R" together form a heterocyclo or heteroaryl ring;
- "aryl" refers to monocyclic or bicyclic aromatic rings having from 6 to 14 atoms, wherein an aryl group contains at least one ring having at least 6 atoms, and wherein the term aryl includes both substituted and unsubstituted aryl groups, wherein aryl groups can optionally be substituted with one or more groups selected from halogen, alkyl, alkoxy, hydroxy, carboxy, carbamoyl, alkyloxycarbonyl, nitro, alkenyloxy, triflouromethyl, amino, cycloalkyl, aryl, heteroaryl, cyano, alkyl, $S(O)_m$ (m=0, 1, 2), and thiol;
- "heteroaryl" refers to pyrrolyl, pyrazolyl, pyrazolinyl, imidazolyl, oxazolyl, diazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl, indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl, carbazolyl, benzidolyl, phenanthrollinyl, acridinyl, phenanthridinyl, or xanthenyl; wherein the heteroaryl can optionally contain one, two or three substituents selected from the group consisting of halo, alkyl, substituted alkyl, alkenyl, alkynyl, aryl, nitro, cyano, hydroxy, alkoxy, thioalkyl, $-CO_2 H$, $-C(=O)H$, $-CO_2$-alkyl, $-C(=O)$alkyl, phenyl, benzyl, phenylethyl, phenyloxy, phenylthio, cycloalkyl, heterocyclo, heteroaryl, $-NR'R''$, $-C(=O)NR'R''$, $-CO_2 NR'R''$, $-C(=O)NR'R''$, $-NR'CO_2 R''$, $-NR'C(=O)R''$, $-SO_2 NR'R''$, and $-NR'SO_2 R''$, wherein each of R' and R" is independently selected from hydrogen, alkyl, and cycloalkyl, or R' and R" together form a heterocyclo or heteroaryl ring;
- "heterocyclic ring" refers to imidazolinyl, thiazolinyl, imidazolindinyl, pyrrolyl, pyrrolinyl, pyranyl, pyrazinyl, piperidyl, morpholinyl, or triazolyl; wherein the heterocyclic ring can be optionally substituted by one or more groups independently selected from alkyl, alkoxy, nitro, monoalkylamino, dialkylamino, cyano, halo, haloalkyl, alkylcarbonyl, $-C(=O)H$, aminocarbonyl, monoalkylaminocarbonyl, dialkylaminocarbonyl, alkyl amido, alkoxyalkyl, alkoxycarbonyl, alkylcarbonyloxy and aryl; and
- "halogen" refers to chlorine, bromine, fluorine or iodine.

2. A compound of claim 1 having Formula 3 or 4:

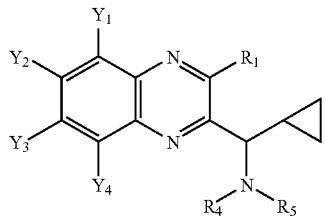

Formula 3

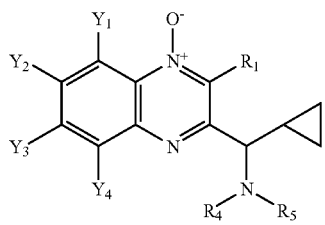

Formula 4 or a pharmaceutically acceptable salt or ester form thereof.

3. A compound of claim 1 having Formula 5 or 6:

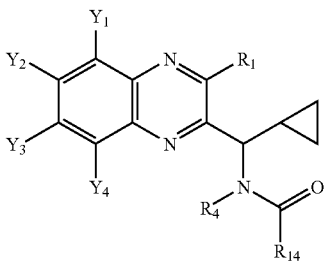

Formula 5

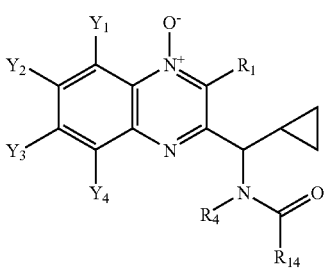

Formula 6 or a pharmaceutically acceptable salt or ester form thereof wherein:

$R_{14}$ is $R_9$, —$OR_{10}$, or $NR_{11}R_{12}$.

4. A compound of claim 3 wherein $R_{14}$ is phenyl or substituted phenyl wherein said substituent is a lower alkyl.

5. A compound of claim 1 wherein $R_1$ is benzyl or methyl.

6. A compound of claim 1 wherein $R_2$ and $R_3$ is cyclopropyl.

7. A compound of claim 6 wherein $R_3$ is cyclopryphyl.

8. A compound of claim 1 wherein n is one.

9. A compound of claim 1 wherein $R_4$ is $(CH_2)_mNR^9R^{10}$ or $(CH_2)_mC(=O)NR^9R^{10}$.

10. A compound of claim 9 wherein $R_4$ is $(CH_2)_mNH_2$ or $(CH_2)_mC(=O)NH_2$.

11. A compound of claim 1 wherein $R_5$ is —C(=O)phenyl optionally substituted with an alkyl group.

12. A compound of claim 11 wherein $R_5$ is —C(=O)phenyl substituted with a methyl group.

13. A compound of claim 1 selected from the group consiting of (±)-N-(3-Amino-propyl)-N-[(3-benzyl-quinoxalin-2-yl)-cyclopropyl-methyl]-4-methylbenzamide or a pharmaceutically acceptable salt or ester form thereof;

(±)-N-(3-Aminopropyl)-N-[(3-benzyl-4-oxyquinoxalin-2-yl)cyclopropylmethyl]-4-methylbenzamide or pharmaceutically acceptable salt or ester form thereof;

(±)-N-(3-Aminopropyl)-N-[(3-benzyl-7-chloroquinoxalin-2-yl)cyclopropyl-methyl]-4-methylbenzamide or a pharmaceutically acceptable salt or ester form thereof;

(±)-N-(3-Aminopropyl)-N-[(3-benzyl-7-chloro-4-oxyquinoxalin-2-yl)cyclopropyl-methyl]-4-methylbenzamide or a pharmaceutically acceptable salt or ester form thereof;

N-[(3-Benzyl-7-chloro-4-oxy-quinoxalin-2-yl)-cyclopropyl-methyl]-N-(2-carbamoyl-ethyl)-4-methyl-benzamide or a pharmaceutically acceptable salt or ester form thereof;

N-(3-Amino-propyl)-N-[(3-butyl-7-chloro-4-oxy-quinoxalin-2-yl)-cyclopropyl-methyl]-4-methyl-benzamide or a pharmaceutically acceptable salt or ester form thereof;

3-[[(3-Benzyl-7-chloro-quinoxalin-2-yl)-cyclopropyl-methyl]-(4-methyl-benzoyl)-amino]-propionic acid methyl ester or pharmaceutically acceptable salt or ester form thereof;

3-[[(3-Benzyl-7-chloro-quinoxalin-2-yl)-cyclopropyl-methyl]-(4-methyl-benzoyl)-amino]-propionic acid or a pharmaceutically acceptable salt or ester form thereof;

N-[(3-Benzyl-7-chloro-quinoxalin-2-yl)-cyclopropyl-methyl]-N-(2-carbamoyl-ethyl)-4-methyl-benzamide or a pharmaceutically acceptable salt or ester form thereof; or 3-[[(3-Benzyl-7-chloro-quinoxalin-2-yl)-cyclopropyl-methyl]-(4-methyl-benzyl)-amino]-propionamide; or a pharmaceutically acceptable salt or ester form thereof.

14. A pharmaceutical composition comprising a compound according to claim 1, or a pharmaceutically acceptable salt thereof.

15. A compound of claim 1, having the formula 3,

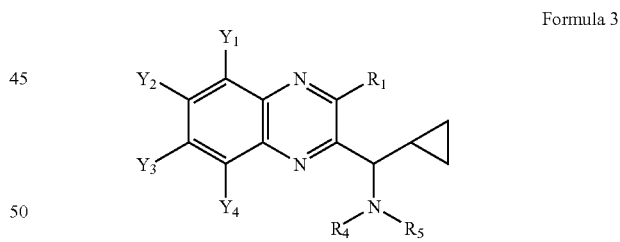

Formula 3 wherein:

$Y_1$, $Y_2$, and $Y_4$ are hydrogen;

$Y_2$ is hydrogen or halogen;

$R_1$ is benzyl or alkyl;

$R_2$ hydrogen;

$R_3$ cycloalkyl;

$R_4$ is —$(CH_2)_mNH_2$ or —$(CH_2)_mC(=O)NH_2$; and $R_5$ is —C(=O)phenyl optionally substituted with a methyl group; or a pharmaceutically-acceptable salt thereof.

16. A pharmeaceutical composition comprising a compound according to claim 15, or a pharmaceutically acceptable salt thereof.

* * * * *

UNITED STATES PATENT AND TRADEMARK OFFICE
CERTIFICATE OF CORRECTION

PATENT NO. : 7,501,416 B2
APPLICATION NO. : 11/047787
DATED : March 10, 2009
INVENTOR(S) : Kyoung Kim et al.

It is certified that error appears in the above-identified patent and that said Letters Patent is hereby corrected as shown below:

In the Claims:

Column 39, line 28, Claim 1, after "salt", delete "or ester form".

Column 39, line 56, Claim 1, after "halo" insert -- , --.

Column 39, line 60, Claim 1, delete "aklenyl" and insert -- alkenyl --.

Column 39, line 60, Claim 1, delete "to" and insert -- to a --.

Column 40, line 7, Claim 1, delete "alkylcarbonlyoxy," and insert -- alkylcarbonyloxy, --.

Column 40, line 12, Claim 1, delete "—C(=O)NR'R"," and insert -- —CO$_2$ NR'R", —C(=O)NR'R", --.

Column 40, lines 17-18, Claim 1, delete "monocyclic or bicyclic aromatic rings having from 6 to 14 atoms," and insert -- a phenyl or napthyl, --.

Column 40, line 25, Claim 1, delete "triflouromethyl," and insert -- trifluoromethyl, --.

Column 40, line 26, Claim 1, delete "aryl," and insert -- phenyl, napthyl, --.

Column 40, line 26, Claim 1, delete "alkyl," and insert -- alkyl --.

Column 40, lines 56-57, Claim 1, delete "imidazolindinyl," and insert -- imidazolidinyl, --.

Column 40, line 58, Claim 1, delete "morpholinyl," and insert -- morpholinyl --.

Column 41, line 23, Claim 2, after "salt", delete "or ester form".

Column 41, line 50, Claim 3, after "salt", delete "or ester form".

Signed and Sealed this

Eighteenth Day of May, 2010

David J. Kappos
*Director of the United States Patent and Trademark Office*

In the Claims:

Column 41, lines 56-57, Claim 6, after "$R_2$" delete "and $R_3$ is cyclopropyl." and insert -- is hydrogen, and $R_3$ is cycloalkyl. --.

Column 41, line 58, Claim 7, delete "cycloprypyl." and insert -- cyclopropyl. --.

Column 42, lines 1-2, Claim 13, delete "consiting" and insert -- consisting --.

Column 42, line 4, Claim 13, after "salt", delete "or ester form".

Column 42, line 6, Claim 13, after "or" insert -- a --.

Column 42, line 7, Claim 13, after "salt", delete "or ester form".

Column 42, line 10, Claim 13, after "salt", delete "or ester form".

Column 42, line 13, Claim 13, after "salt", delete "or ester form".

Column 42, line 17, Claim 13, after "salt", delete "or ester form".

Column 42, line 21, Claim 13, after "salt", delete "or ester form".

Column 42, line 25, Claim 13, delete "or" and insert -- or a --.

Column 42, lines 25-26, Claim 13, after "salt", delete "or ester form".

Column 42, line 29, Claim 13, after "salt", delete "or ester form".

Column 42, line 32, Claim 13, after "salt", delete "or ester form".

Column 42, line 36, Claim 13, after "salt", delete "or ester form".

Column 42, line 57, Claim 15, delete "$R_2$" and insert -- $R_2$ is --.

Column 42, line 58, Claim 15, delete "$R_3$" and insert -- $R_3$ is --.

Column 42, line 62, Claim 16, delete "pharmeaceutical" and insert -- pharmaceutical --.